(12) United States Patent
Goudy et al.

(10) Patent No.: US 10,307,300 B2
(45) Date of Patent: *Jun. 4, 2019

(54) APPARATUS AND METHODS FOR TRANSFERRING AND BONDING SUBSTRATES

(71) Applicant: The Procter & Gamble Company, Cincinnati, OH (US)

(72) Inventors: Eric Shawn Goudy, Liberty Township, OH (US); Jason Lee DeBruler, West Chester, OH (US); Michael Devin Long, Springfield Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 325 days.

This patent is subject to a terminal disclaimer.

(21) Appl. No.: 15/373,634

(22) Filed: Dec. 9, 2016

(65) Prior Publication Data

US 2017/0165120 A1 Jun. 15, 2017

Related U.S. Application Data

(60) Provisional application No. 62/300,114, filed on Feb. 26, 2016, provisional application No. 62/265,443, filed on Dec. 10, 2015.

(51) Int. Cl.
*A61F 13/15* (2006.01)
*B29C 65/00* (2006.01)
(Continued)

(52) U.S. Cl.
CPC ........ *A61F 13/15739* (2013.01); *B29C 65/02* (2013.01); *B29C 65/48* (2013.01);
(Continued)

(58) Field of Classification Search
CPC ..... A61F 13/15739; A61F 2013/15878; Y10T 156/1054; B29L 2031/4878;
(Continued)

(56) References Cited

U.S. PATENT DOCUMENTS 3,860,003 A 1/1975 Buell
4,610,678 A 9/1986 Weisman et al.
(Continued)

FOREIGN PATENT DOCUMENTS

EP 0 844 062 A1 5/1998
EP 2 796 271 A1 10/2014
(Continued)

OTHER PUBLICATIONS

PCT International Search Report, dated Mar. 1, 2017, 11 pages.
(Continued)

*Primary Examiner* — Carson Gross
(74) *Attorney, Agent, or Firm* — Andrew J. Hagerty; Charles R. Matson; Sarah M. DeCristofaro

(57) ABSTRACT

A substrate assembly is mechanically deformed to form various products. In part, the substrate assembly may advance toward a bonder apparatus. The bonder apparatus rotates about a longitudinal axis and includes a plurality of manifolds. The plurality of manifolds allow for substrate assemblies including different process product pitches to be processed on a single bonder apparatus.

2 Claims, 20 Drawing Sheets

(51) Int. Cl.
    *B29C 65/02*     (2006.01)
    *B29C 65/10*     (2006.01)
    *B29C 65/48*     (2006.01)
    *B29L 31/48*     (2006.01)

(52) U.S. Cl.
    CPC .......... *B29C 66/00* (2013.01); *B29C 66/7294* (2013.01); *A61F 2013/15829* (2013.01); *A61F 2013/15878* (2013.01); *B29C 65/10* (2013.01); *B29C 66/83411* (2013.01); *B29C 66/83511* (2013.01); *B29L 2031/4871* (2013.01); *B32B 2555/02* (2013.01); *Y10T 156/1054* (2015.01)

(58) Field of Classification Search
    CPC ................ B32B 2555/02; B29C 65/10; B29C 66/83411; B29C 66/83511
    See application file for complete search history.

(56) References Cited

U.S. PATENT DOCUMENTS

| | | | |
|---|---|---|---|
| 4,673,402 A | 6/1987 | Weisman et al. | |
| 4,695,278 A | 9/1987 | Lawson | |
| 4,704,115 A | 11/1987 | Buell | |
| 4,795,454 A | 1/1989 | Dragoo | |
| 4,834,735 A | 5/1989 | Alemany et al. | |
| 4,888,231 A | 12/1989 | Angstadt | |
| 4,909,803 A | 3/1990 | Aziz et al. | |
| 5,562,646 A | 10/1996 | Goldman et al. | |
| 5,628,097 A | 5/1997 | Benson et al. | |
| 5,669,894 A | 9/1997 | Goldman et al. | |
| 5,916,661 A | 6/1999 | Benson et al. | |
| 6,107,539 A | 8/2000 | Palumbo et al. | |
| 6,545,197 B1 | 4/2003 | Muller et al. | |
| 6,790,798 B1 | 9/2004 | Suzuki et al. | |
| 7,569,039 B2 | 8/2009 | Matsuda et al. | |
| 7,587,966 B2 | 9/2009 | Nakakado et al. | |
| 8,778,127 B2 | 7/2014 | Schneider et al. | |
| 2004/0097895 A1 | 5/2004 | Busam et al. | |
| 2004/0158212 A1 | 8/2004 | Ponomarenko et al. | |
| 2005/0107764 A1 | 5/2005 | Matsuda et al. | |
| 2009/0312730 A1 | 12/2009 | LaVon et al. | |
| 2012/0061015 A1 | 3/2012 | LaVon et al. | |
| 2012/0061016 A1 | 3/2012 | LaVon et al. | |
| 2013/0213547 A1* | 8/2013 | Schneider ........... | A61F 13/4963 156/60 |
| 2013/0218116 A1* | 8/2013 | Schneider ........... | A61F 13/4963 604/385.01 |
| 2013/0255861 A1 | 10/2013 | Schneider | |
| 2013/0255862 A1 | 10/2013 | Schneider et al. | |
| 2013/0255863 A1 | 10/2013 | LaVon et al. | |
| 2013/0255864 A1 | 10/2013 | Schneider et al. | |
| 2013/0255865 A1 | 10/2013 | Brown et al. | |
| 2014/0110053 A1 | 4/2014 | Ordway et al. | |
| 2014/0305593 A1 | 10/2014 | Schneider et al. | |
| 2017/0027763 A1* | 2/2017 | Fujita .................. | B29C 66/8412 |

FOREIGN PATENT DOCUMENTS

| | | |
|---|---|---|
| WO | WO 2013/126480 A1 | 8/2013 |
| WO | WO 2016/126952 A1 | 8/2016 |

OTHER PUBLICATIONS

PCT International Search Report, dated Mar. 9, 2017, 13 pages.
PCT International Search Report, dated Mar. 9, 2017, 12 pages.
U.S. Appl. No. 15/373,508, filed Dec. 9, 2016, Goudy, et al.
U.S. Appl. No. 15/373,842, filed Dec. 9, 2016, Goudy, et al.

\* cited by examiner

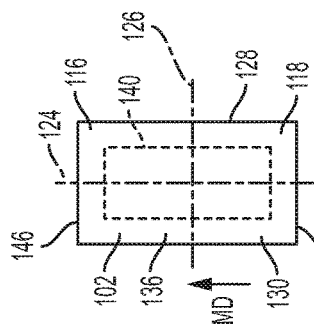
FIG. 5B1
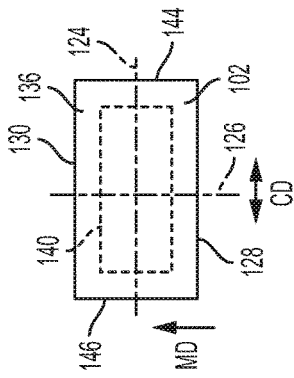
FIG. 5B2
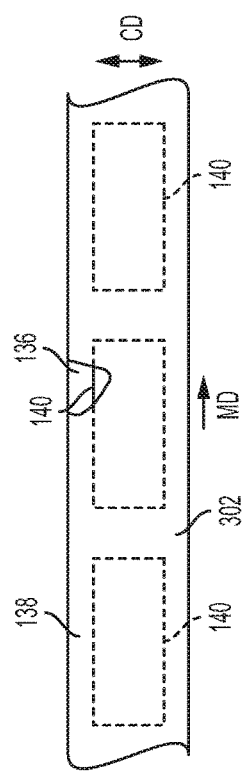
FIG. 5A
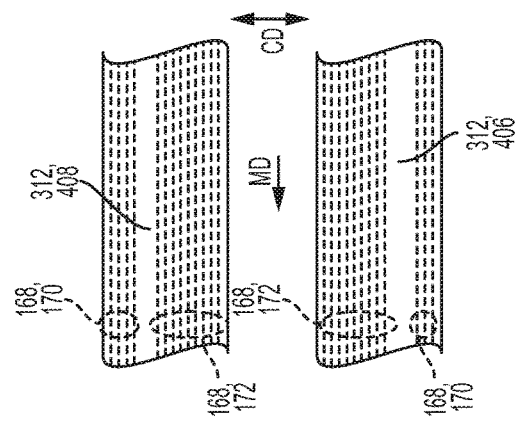
FIG. 5C

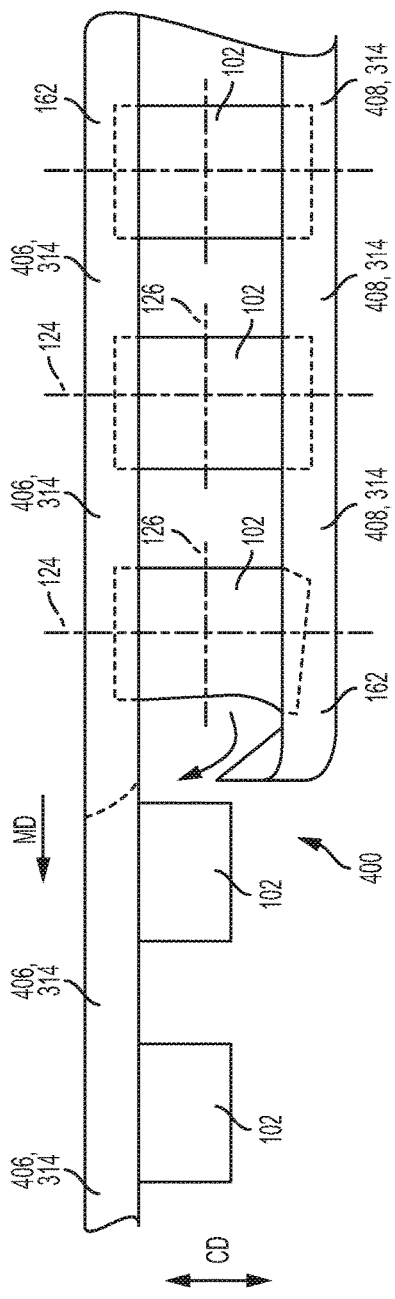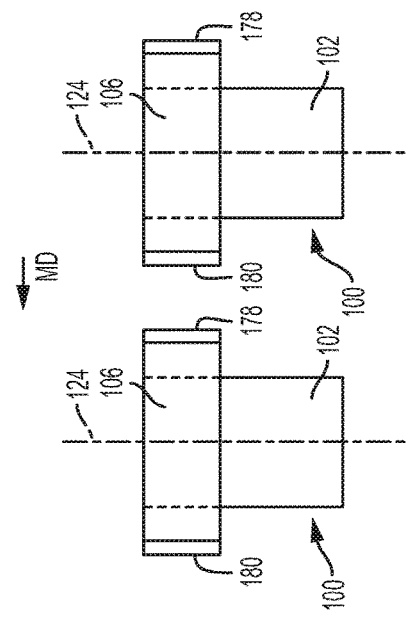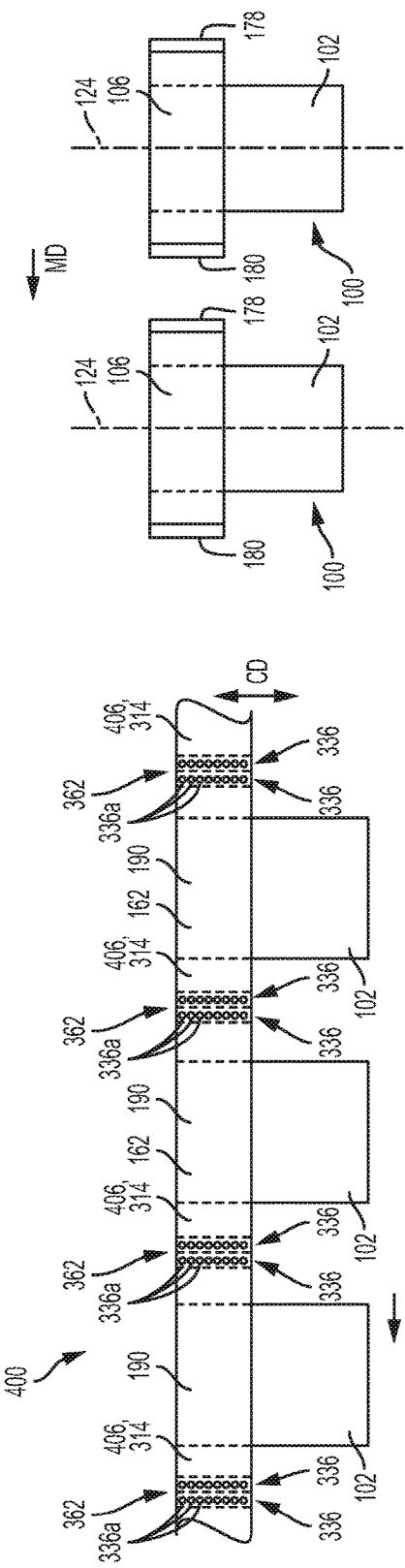

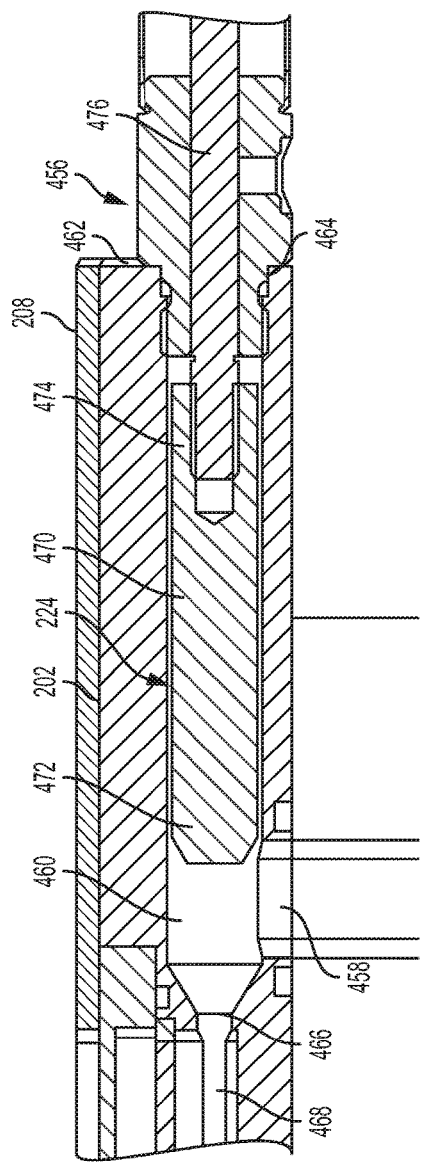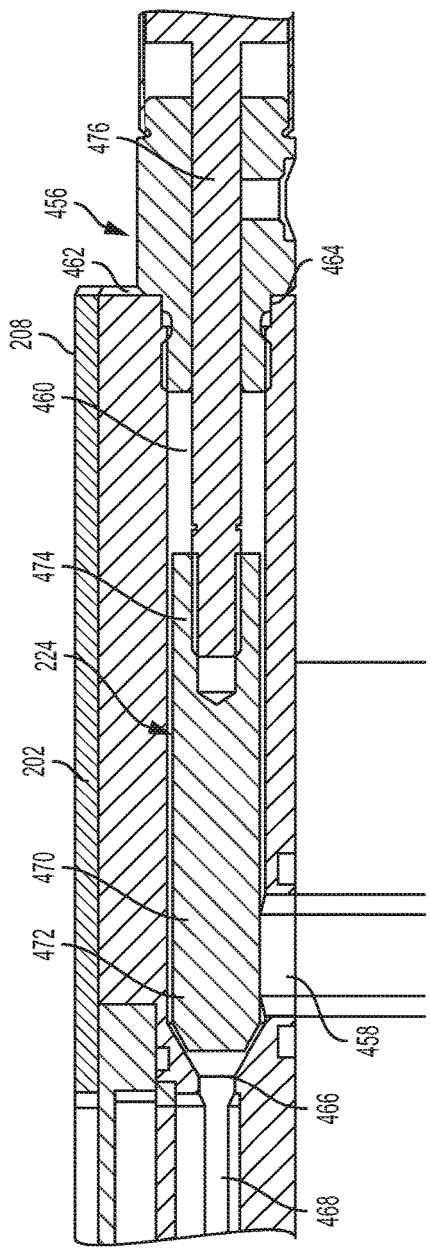

APPARATUS AND METHODS FOR TRANSFERRING AND BONDING SUBSTRATES

TECHNICAL FIELD

The present disclosure relates to methods for manufacturing absorbent articles, and more particularly, to apparatuses and methods for bonding two or more partially meltable materials.

BACKGROUND

Disposable absorbent articles, in particular, disposable diapers, are designed to be worn by people experiencing incontinence, including infants and invalids. Such diapers are worn about the lower torso of the wearer and are intended to absorb and contain urine and other bodily discharges, thus preventing the soiling, wetting, or similar contamination of articles that may come into contact with a diaper during use (e.g., clothing, bedding, other people, etc.). Disposable diapers are available in the form of pull-on diapers, also referred to as training pants, having fixed sides, or taped diapers having unfixed sides.

Along an assembly line, various types of articles, such as diapers and other absorbent articles, may be assembled by adding components to and/or otherwise modifying an advancing, continuous web of material. In some processes, advancing webs of material are combined with other advancing webs of material. In other processes, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

In some converting configurations, discrete chassis spaced apart from each other are advanced in a machine direction and are arranged with a longitudinal axis parallel with the cross direction. Opposing waist regions of discrete chassis are then connected with continuous lengths of elastically extendable front and back belt webs advancing in the machine direction. While connected with the chassis, the front and back belt webs are maintained in a fully stretched condition along the machine direction, forming a continuous length of absorbent articles. The continuous length of absorbent articles may then be folded in a cross direction. During the folding process in some converting configurations, one of the front and back belt webs is folded into a facing relationship with the opposing belt. The front and back belts may then be bonded together to create the side seams on diapers.

Absorbent articles, such as diapers which may be worn by infants and adults, come in a variety of sizes. Thus, one absorbent article may include a larger chassis and a larger belt as compared to another absorbent article which may include a smaller chassis and a smaller belt. The manufacturing process for these absorbent articles is desired to be such that the absorbent article including the larger chassis and the larger belt can be manufactured on the same equipment or similar equipment as the absorbent article including the smaller chassis and the smaller belt. Having to switch out equipment or to make large modifications to the equipment for manufacturing different sized articles is costly and time consuming for manufacturers.

Thus, it would be beneficial to provide an apparatus and a method for transferring and bonding absorbent articles of different sizes.

SUMMARY

Aspects of the present disclosure involve apparatuses and methods for manufacturing absorbent articles, and more particularly, methods for mechanically deforming substrates during the manufacture of disposable absorbent articles. Particular embodiments of methods of manufacture disclosed herein provide for forming side seams in various types of diaper configurations. It is to be appreciated that the methods and apparatuses disclosed herein can also be applied to other mechanical deformation used on diapers as well as other types of absorbent articles.

In one embodiment, an apparatus for bonding one or more substrates includes the following. A heat member configured to heat a fluid. A plurality of manifolds may be fluidly connected to the heat member. The plurality of manifolds may be positioned about a central longitudinal axis, and each of the plurality of manifolds includes a first end portion and a second end portion opposite the first end portion. Each of the plurality of manifolds may include a fluid opening and a control chamber defined by the manifold and extending from the fluid opening to the first end portion of the manifold. Each manifold may also include a fluid chamber fluidly connected to the control chamber. The fluid chamber may extend from the control chamber toward the second end portion of the manifold. A nozzle plate may extend along the fluid chamber, and the nozzle plate may be fluidly connected to the fluid chamber. A support plate may be positioned adjacent the nozzle plate. The support plate may define a first slot configured to substantially encircle a portion of the nozzle plate. The apparatus may also include a plurality of actuators adjacent the plurality of manifolds. Each of the plurality of actuators may be configured to engage an engagement member. The engagement member is slidably engaged with the control chamber. Further, the engagement member includes a proximal end portion and a distal end portion opposite the proximal end portion. The engagement member may be positioned in a first configuration and a second configuration. In the first configuration, a portion of the engagement member may be disposed over the fluid opening and the proximal end portion of the engagement member may be positioned adjacent to the fluid chamber such that the engagement member prevents the fluid from entering the fluid chamber. In the second configuration, the proximal end portion of the engagement member may be positioned adjacent the fluid chamber such that the fluid flows from the control chamber into the fluid chamber.

In another embodiment, a method for forming a bond, the method includes the steps of: advancing a substrate assembly in a machine direction, wherein the substrate assembly comprises a process product pitch defined by a leading portion and a trailing portion, and a central portion between the leading portion and the trailing portion; rotating a bonder apparatus about an axis of rotation, wherein the bonder apparatus comprises a plurality of manifolds disposed about a central longitudinal axis, and wherein each of the plurality of manifolds comprises a support plate and a nozzle plate adjacent the support plate, wherein the nozzle plate defines a plurality of apertures; receiving the leading portion of the substrate on the support plate of a first manifold; receiving the trailing portion of the substrate on the support plate of a second manifold, wherein the central portion of the substrate is disposed on the support plates of the portion of the plurality of manifolds between each of the first manifold and the second manifold; heating a fluid to form a heated fluid; supplying the heated fluid to the plurality of manifolds; releasing the heated fluid through the plurality of apertures defined by the nozzle plate of the first manifold such that the heated fluid engages the leading portion; releasing the heated fluid through the plurality of apertures defines by the nozzle plate of the second manifold such that the heated fluid engages the trailing portion; and bonding at least a portion of the substrate assembly.

In another embodiment, a method for forming a bond, the method comprising the steps of: advancing a substrate assembly in a machine direction at a process product pitch, wherein the substrate assembly comprises a process product pitch defined by a leading portion and a trailing portion, and a central portion between the leading portion and the trailing portion; rotating a bonder apparatus about an axis of rotation, wherein the bonder apparatus comprises a plurality of manifolds disposed about a central longitudinal axis, and wherein each of the plurality of manifolds includes a nozzle plate defining a plurality of apertures; expanding or contracting the substrate assembly such that the substrate assembly is advanced at a second process product pitch, wherein the second process product pitch is greater than or less than the process product pitch; receiving the leading portion of the substrate on a first manifold; receiving the trailing portion of the substrate on a second manifold, wherein the central portion of the substrate is disposed on the portion of the plurality of manifolds between each of the first manifold and the second manifold; heating a fluid to form a heated fluid; supplying the heated fluid to the plurality of manifolds; releasing the heated fluid through the plurality of apertures defined by the nozzle plate of the first manifold such that the heated fluid engages the leading portion; releasing the heated fluid through the plurality of apertures defined by the nozzle plate of the second manifold such that the heated fluid engages the trailing portion; and bonding at least a portion of the substrate assembly.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 5A is a top view of a chassis assembly taken along line 5A-5A of FIG. 4 in accordance with one non-limiting embodiment of the present disclosure;

FIG. 5B1 is a top view of a discrete chassis taken along line 5B1-5B1 of FIG. 4 in accordance with one non-limiting embodiment of the present disclosure;

FIG. 5B2 is a top view of a discrete chassis taken along line 5B2-5B2 of FIG. 4 in accordance with one non-limiting embodiment of the present disclosure;

FIG. 5C is a top view of elastic belt substrates taken along line 5C-5C of FIG. 4 in accordance with one non-limiting embodiment of the present disclosure;

FIG. 5D is a top view of multiple discrete chassis attached to a first elastic belt substrate and a second elastic belt substrate taken along line 5D-5D of FIG. 4 in accordance with one non-limiting embodiment of the present disclosure;

FIG. 5E is a top view of multiple discrete chassis attached to a substrate assembly taken along line 5E-5E of FIG. 4 in accordance with one non-limiting embodiment of the present disclosure;

FIG. 5F is a top view of two discrete absorbent articles taken along line 5F-5F of FIG. 4 in accordance with one non-limiting embodiment of the present disclosure;

FIG. 9A is a partially cut-away, detailed side view of a portion of a manifold operatively engaged with an actuator in accordance with one non-limiting embodiment of the present disclosure;

FIG. 9B is a partially cut-away, detailed side view of a portion of a manifold operatively engaged with an actuator in accordance with one non-limiting embodiment of the present disclosure;

DETAILED DESCRIPTION

Figure 1:
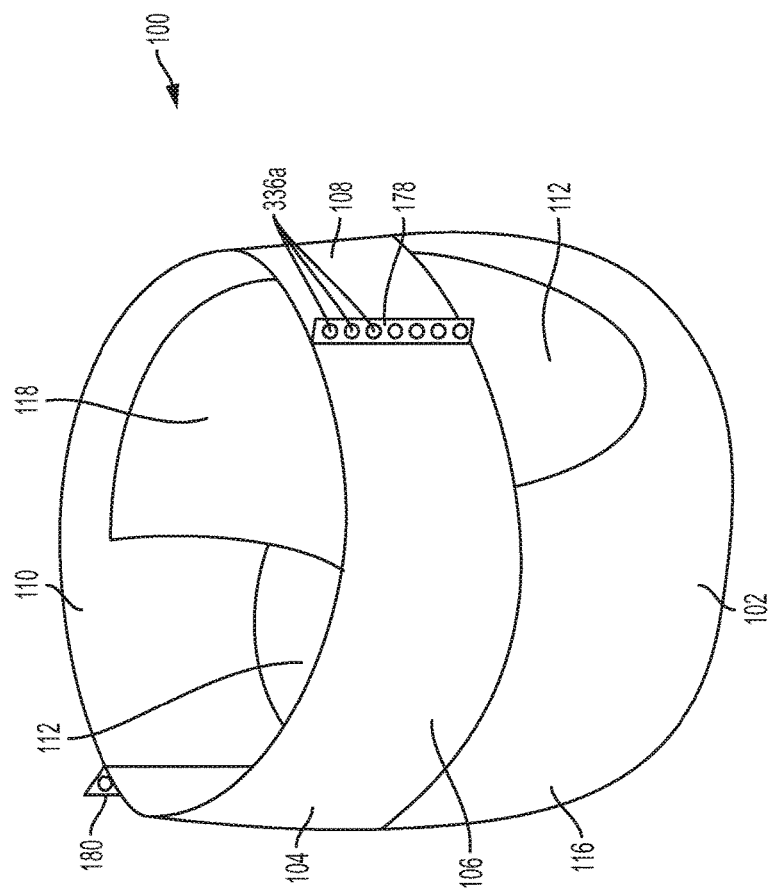
FIG. 1 is a perspective view of a diaper pant.

The methods and apparatuses described herein relate to transferring and bonding substrates. In general, portions of substrates may be overlapped and a jet of heated fluid is delivered from an aperture to at least partially melt the overlapping substrate portions. More particularly, the jet of heated fluid penetrates the substrate portions and at least partially melts the overlapping substrate portions where the substrate portions interface at an overlap area. The location of the substrate portions relative to the heated fluid may be controlled such that the substrate portions are held a predetermined distance away from the heating operation. Pressure may then be applied at the overlap area thereby joining the substrate portions together. In all the embodiments described herein, the fluid may include ambient air or other gases.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

As used herein, the term "joining" describes a configuration whereby a first element is directly secured to another element by affixing the first element directly to the other element.

As used herein, the term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a substrate, layer or layers of fibrous materials, nonwovens, films and foils such as polymeric films or metallic foils. These materials may be used alone or may comprise two or more layers laminated together. As such, a web is a substrate.

The term "elongatable," "extensible," or "stretchable" are used interchangeably and refer to a material that, upon application of a biasing force, can stretch to an elongated length of at least 130% of its relaxed, original length (i.e. can stretch to 30% more than its original length), without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend to 150 mm, and upon removal of the force retracts to a length of at least 130 mm (i.e., exhibiting a 40% recovery).

As used herein, the term "pull-on diaper" refers to a garment that is generally worn by infants and sufferers of incontinence, which is pulled on like pants. It should be understood, however, that the present disclosure is also applicable to other absorbent articles, such as taped diapers, incontinence briefs, feminine hygiene garments, and the like, including absorbent articles intended for use by infants, children, and adults.

As used herein, the term "at least partially melted" refers to materials at least a portion of which have reached at least a softening point temperature, but have not reached a melt point temperature. "Melted" also refers, in its ordinary sense, to materials which have exceeded their melt point temperatures over at least a portion of the material. "Meltable" refers to materials that at least soften when heated or when some other energy is applied or generated.

The present disclosure relates to methods and apparatuses for bonding substrates together. Generally, the bonder apparatus is rotated about an axis of rotation and a substrate assembly may be advanced in a machine direction and received on the bonder apparatus. The bonder apparatus may include a plurality of manifolds positioned about the axis of rotation. A fluid may be supplied to one or more manifolds such that a portion of the substrate assembly is heated and the one or more layers of the substrate assembly may be bonded. Further, in some embodiments, the substrate assembly may be compressed.

As discussed below, the bonder apparatus may be configured to partially melt and/or compress the substrates while traveling on the bonder apparatus. More specifically, the bonder apparatus may include a plurality of manifolds positioned about the axis of rotation. Further, as previously discussed, absorbent articles may be produced in a number of different sizes. Thus, the belt of the absorbent article may be bonded at any number of positions based on the intended size of the absorbent article. The plurality of manifolds allow for a number of different sized absorbent articles to be processed, such as by joining one or more substrates. For example, a substrate assembly having a first size is advanced onto the bonder apparatus. Based on the desired size, the substrate assembly will need to be joined at a first location and a second location. These locations coincide with certain manifolds. More specifically, the first location of the substrate assembly may be disposed on a first manifold and the second location of the substrate assembly may be disposed on the second manifold. A fluid is heated to a temperature sufficient to at least partially melt the portions of the substrate assembly corresponding to the first and second locations. As the bonder apparatus rotates, the heated fluid is supplied to the first manifold and the second manifold and is released through the apertures defined by the first and second manifolds. The portions of the substrate assembly disposed on the first and second manifolds may be partially melted. It is to be appreciated that the manifolds located between the first and second manifolds may not release heated fluid. Only those manifolds that have portions of the substrate assembly disposed thereon that are intended to be partially melted are activated by releasing fluid. It is also to be appreciated that each manifold may be individually controlled such that any combination of manifolds may be activated, release heated fluid, at any given time. The partially melted area may then be compressed, creating a discrete bond region or seam. The bonder apparatus continues to rotate and the substrate assembly may be removed from the bonder apparatus and advanced to subsequent processes. It is to be appreciated that the partially melted area may be compressed while disposed on the bonder apparatus or after being removed from the bonder apparatus.

As described in greater detail below, a seam may be formed between at least two substrate layers, each substrate layer comprising one or more meltable components. A seam may also be formed between portions of the same substrate that is, for example, folded along a fold line formed between two substrate portions. The substrate portions to be bonded may be positioned adjacent one another.

It is to be appreciated that although the transfer and bonding methods and apparatuses herein may be configured to bond various types of substrates, the methods and apparatuses herein are discussed below in the context of manufacturing absorbent articles. In particular, the methods and apparatuses are discussed in the context of bonding substrates, such as belts, together to form side seams of advancing, continuous lengths of absorbent articles during production. As discussed below, an advancing continuous length of absorbent articles may include a plurality of chassis connected with a continuous first substrate and a continuous second substrate.

Prior to the bonder apparatus, continuous first and second substrates may be separated from each other along a cross direction while advancing along a machine direction MD. Each chassis may extend in the cross direction CD and may include opposing first and second end regions separated by a central region, wherein the first end regions are connected with the first substrate and the second end regions are connected with the second substrate. The chassis may also be spaced from each other along the machine direction MD. A folding apparatus operates to fold the chassis around the folding axis along the central regions and to bring the second substrate and second end region of the chassis into a facing relationship with the first substrate and first end region of the chassis. The first substrate and the second substrate positioned in a facing relationship form a substrate assembly. The substrate assembly and the folded chassis advance in the machine direction onto the bonder apparatus such as described above.

The methods and apparatuses discussed herein may be used to bond various types of substrate configurations, some of which may be used in the manufacture of different types of absorbent articles. To help provide additional context to the subsequent discussion of the process embodiments, the following provides a general description of absorbent articles in the form of diapers that include components that may be bonded in accordance with the methods and apparatuses disclosed herein.

Figure 2:
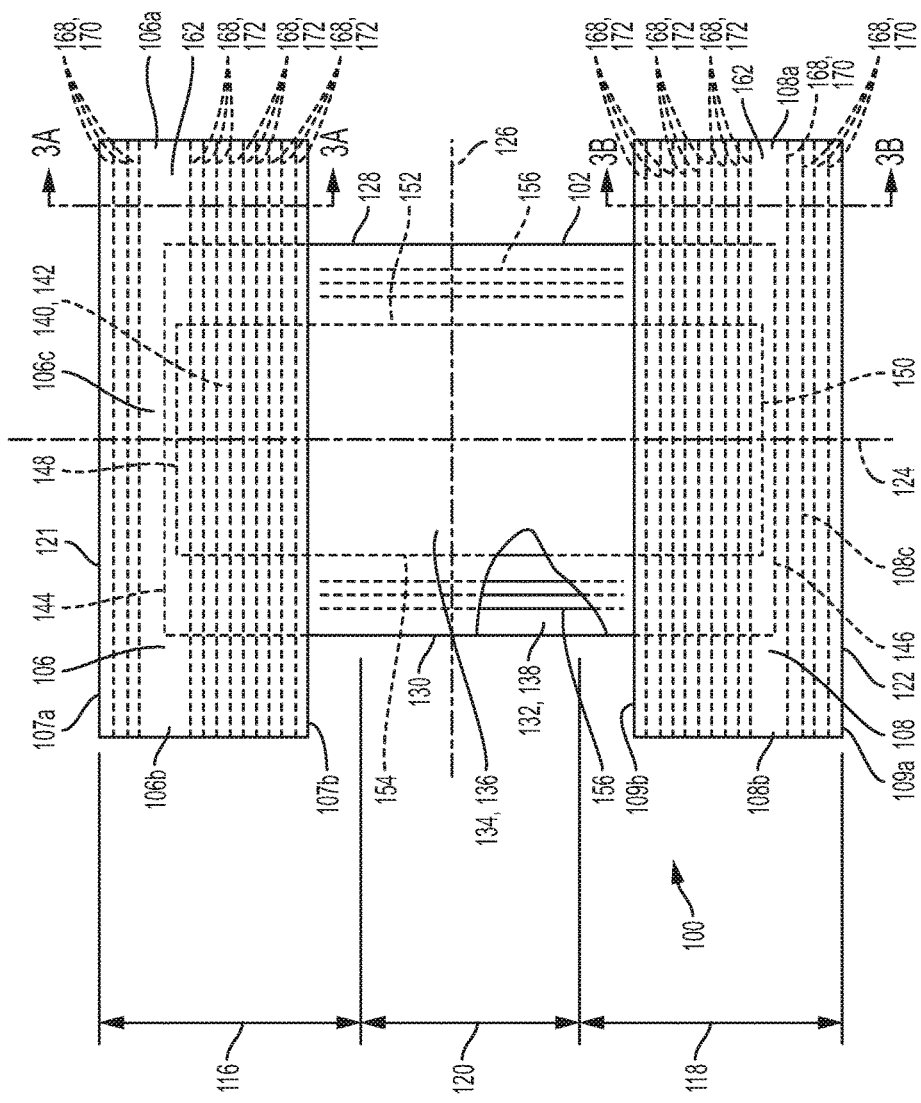
FIG. 2 is a partially cut away plan view of the diaper pant shown in FIG. 1.

FIGS. 1 and 2 show an example of a diaper pant 100 that may be transferred and/or bonded with the apparatuses and methods disclosed herein. In particular, FIG. 1 shows a perspective view of a diaper pant 100 in a pre-fastened configuration, and FIG. 2 shows a plan view of the diaper pant 100 with the portion of the diaper that faces away from a wearer oriented towards the viewer. The diaper pant 100 shown in FIGS. 1 and 2 includes a chassis 102 and a ring-like elastic belt 104. As discussed below in more detail, a first elastic belt 106 and a second elastic belt 108 are connected together to form the ring-like elastic belt 104.

With continued reference to FIG. 2, the chassis 102 includes a first waist region 116, a second waist region 118, and a crotch region 119 disposed intermediate the first and second waist regions. The first waist region 116 may be configured as a front waist region, and the second waist region 118 may be configured as back waist region. In some embodiments, the length of each of the front waist region, back waist region, and crotch region 120 may be ⅓ of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the diaper 100 and chassis 102 of FIG. 2 is shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1 and 2, the diaper pant 100 may include an inner, body facing surface 132, and an outer, garment facing surface 134. The chassis 102 may include a backsheet 136 and a topsheet 138. The chassis 102 may also include an absorbent assembly 140 including an absorbent core 142 that may be disposed between a portion of the topsheet 138 and the backsheet 136. As discussed in more detail below, the diaper 100 may also include other features, such as leg elastics and/or leg cuffs to enhance the fit around the legs of the wearer.

As shown in FIG. 2, the periphery of the chassis 102 may be defined by the first longitudinal side edge 128, a second longitudinal side edge 130; a first laterally extending end edge 144 disposed in the first waist region 116; and a second laterally extending end edge 146 disposed in the second waist region 118. Both side edges 128 and 130 extend longitudinally between the first end edge 144 and the second end edge 146. As shown in FIG. 2, the laterally extending end edges 144 and 146 are located longitudinally inward from the laterally extending front waist edge 121 in the front waist region 116 and the laterally extending back waist edge 122 in the back waist region 118. When the diaper pant 100 is worn on the lower torso of a wearer, the front waist edge 121 and the back waist edge 122 of the chassis 102 may encircle a portion of the waist of the wearer. At the same time, the chassis side edges 128 and 130 may encircle at least a portion of the legs of the wearer. And the crotch region 120 may be generally positioned between the legs of the wearer with the absorbent core 142 extending from the front waist region 116 through the crotch region 120 to the back waist region 118.

It is also to be appreciated that a portion or the whole of the diaper 100 may also be made laterally extensible. The additional extensibility may help allow the diaper 100 to conform to the body of a wearer during movement by the wearer. The additional extensibility may also help, for example, allow the user of the diaper 100 including a chassis 102 having a particular size before extension to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper pant 100 may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100, such as bedsheets, pajamas, and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper pant 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916, 661; 6,545,197; and 6,107,539.

As mentioned above, the diaper pant 100 may also include an absorbent assembly 140 that is joined to the chassis 102.

As shown in FIG. 2, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834, 735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/ 0097895.

As previously mentioned, the diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695, 278; 4,795,454; 4,704,115; 4,909,803; U.S. Patent Publication No. 2009/0312730 A1; and U.S. Patent Publication No. 2013/0255865 A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIG. 1. As previously mentioned, the ring-like elastic belt 104 is defined by a first elastic belt 106 connected with a second elastic belt 108. As shown in FIG. 2, the first elastic belt 106 defines first and second opposing end regions 106a, 106b and a central region 106c, and the second elastic 108 belt defines first and second opposing end regions 108a, 108b and a central region 108c.

The central region 106c of the first elastic belt is connected with the first waist region 116 of the chassis 102, and the central region 108c of the second elastic belt 108 is connected with the second waist region 118 of the chassis 102. As shown in FIG. 1, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

Figure 3A:
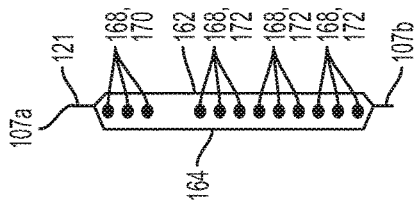
FIG. 3A is a cross-sectional view of the diaper pant of FIG. 2 taken along line 3A-3A of FIG. 2.
Figure 3B:
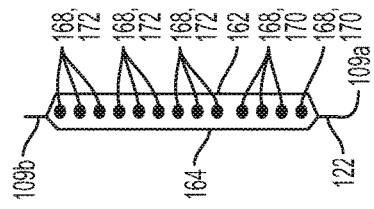
FIG. 3B is a cross-sectional view of the diaper pant of FIG. 2 taken along line 3B-3B of FIG. 2.

As shown in FIGS. 2, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 109a may also define the front waist edge 121 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts may include a nonwoven web of synthetic fibers, and may include a stretchable nonwoven. In other embodiments, the first and second elastic belts may include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, or panels extending along the lengths of the elastic belts. As shown in FIGS. 2, 3A, and 3B, the belt elastic material may include a plurality of elastic strands 168 that may be referred to herein as outer, waist elastics 170 and inner, waist elastics 172.

As shown in FIG. 2, the outer, waist elastics 170 extend continuously laterally between the first and second opposing end regions 106a, 106b and across the central region 106c of the first elastic belt 106 and between the first and second opposing end regions 108a, 108b and across the central region 108c of the second elastic belt 108. In some embodiments, some elastic strands 168 may be configured with discontinuities in areas. For example, as shown in FIG. 2, the inner, waist elastics 172 extend intermittently along the first and second elastic belts 106, 108. More particularly, the inner, waist elastics 172 extend along the first and second opposing end regions 106a, 106b and partially across the central region 106c of the first elastic belt 106. The inner, waist elastics 172 also extend along the first and second opposing end regions 108a, 108b and partially across the central region 108c of the second elastic belt 108. As such, the inner, waist elastics 172 do not extend across the entirety of the central regions 106c, 108c of the first and second elastic belts 106, 108. Thus, some elastic strands 168 may not extend continuously through regions of the first and second elastic belts 106, 108 where the first and second elastic belts 106, 108 overlap the absorbent assembly 140. In some embodiments, some elastic strands 168 may partially extend into regions of the first and second elastic belts 106, 108 where the first and second elastic belts 106, 108 overlap the absorbent assembly 140. In some embodiments, some elastic strands 168 may not extend into any region of the first and second elastic belts 106, 108 where the first and second elastic belts 106, 108 overlap the absorbent assembly 140. It is to be appreciated that the first and/or second elastic belts 106, 108 may be configured with various configurations of discontinuities in the outer, waist elastics 170 and/or the inner, waist elastic elastics 172.

In some embodiments, the elastic strands 168 may be disposed at a constant interval in the longitudinal direction. In other embodiments, the elastic strands 168 may be disposed at different intervals in the longitudinal direction. As discussed in more detail below, the belt elastic strands 168, in a stretched condition, may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2.

As previously mentioned, the apparatuses and methods according to the present disclosure may be utilized to transfer and/or bond discrete absorbent articles 100 and/or various components of absorbent articles 100, such as for example, chassis 102, elastic belts 106, 108, and/or leg cuffs 156. Although the following methods may be provided in the context of the diaper 100 shown in FIGS. 1 and 2, it is to be appreciated that the methods and apparatuses herein may be used with various process configurations and/or absorbent articles, such as for example, disclosed in U.S. Pat. No. 7,569,039; U.S. Patent Publication Nos. 2005/0107764 A1, 2012/0061016 A1, and 2012/0061015 A1; 2013/0255861 A1; 2013/0255862 A1; 2013/0255863 A1; 2013/0255864 A1; and 2013/0255865 A1.

Figure 4:
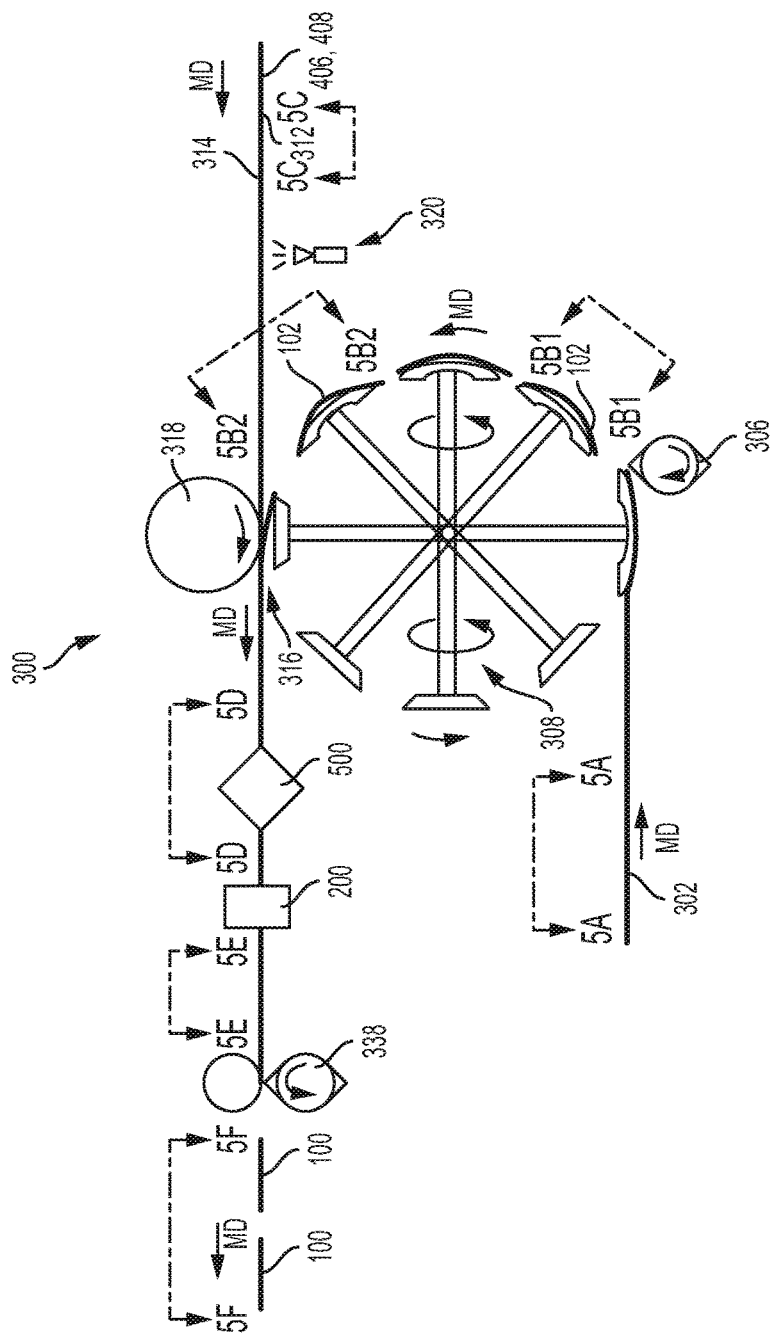
FIG. 4 is a schematic representation of a converting apparatus in accordance with one non-limiting embodiment of the present disclosure.

As previously mentioned, the apparatuses and methods according to the present disclosure may be utilized to assemble various components of absorbent articles 100. For example, FIG. 4 shows a schematic view of a converting apparatus 300 adapted to manufacture absorbent articles 100. The method of operation of the converting apparatus 300 may be described with reference to the various components of absorbent articles 100, such as described above and shown in FIGS. 1 and 2. Although the following methods are provided in the context of the absorbent article 100 shown in FIGS. 1 and 2, it is to be appreciated that various embodiments of diaper pants can be manufactured according to the methods disclosed herein, such as for example, the absorbent articles disclosed in U.S. Pat. No. 7,569,039 and U.S. Patent Publication Nos. 2005/0107764 A1; 2012/0061016 A1; and 2012/0061015 A1.

As described in more detail below, the converting apparatus 300 shown in FIG. 4 operates to advance discrete chassis 102 along a machine direction MD such that the lateral axis of each chassis 102 is parallel with the machine direction, and wherein the chassis 102 are spaced apart from each other along the machine direction. Opposing waist regions 116, 118 of the spaced apart chassis 102 are then connected with continuous lengths of advancing first and second substrates 406, 408, as illustrated in FIGS. 5B1 and 5C. The chassis 102 are then folded along the lateral axis to bring the first and second substrates 406, 408 into a facing relationship, as illustrated in FIG. 5D, and the first and second substrates are connected together along regions 336 intermittently spaced along the machine direction MD, wherein each region 336 may include one or more discrete bond sites 336a, as illustrated in FIG. 5E. And the substrates 406, 408 are cut along the regions 336 to form a discrete belt and creating discrete absorbent articles 100, such as shown in FIG. 1.

As shown in FIGS. 4 and 5A, a continuous length of chassis assemblies 302 are advanced in a machine direction MD to a carrier apparatus 308 and cut into discrete chassis 102 with knife roll 306. The continuous length of chassis assemblies 302 may include absorbent assemblies 140 sandwiched between topsheet material 138 and backsheet material 136, leg elastics, barrier leg cuffs and the like.

After the discrete absorbent chassis 102 are cut by the knife roll 306, the carrier apparatus 308 rotates and advances the discrete chassis 102 in the machine direction MD in the orientation shown in FIG. 5B1, wherein the longitudinal axis 124 of the chassis 102 is generally parallel with the machine direction MD. While the chassis 102 shown in FIG. 5B1 is shown with the second laterally extending end edge 146 as a leading edge and the first laterally extending end edge 144 as the trailing edge, it is to be appreciated that in other embodiments, the chassis 102 may be advanced in other orientations. For example, the chassis may be oriented such that the second laterally extending end edge 146 is a trailing edge and the first laterally extending end edge 144 is a leading edge. The carrier apparatus 308 also rotates while at the same time changing the orientation of the advancing chassis 102. The carrier apparatus 308 may also change the speed at which the chassis 102 advances in the machine direction MD. It is to be appreciated that various forms of carrier apparatuses may be used with the methods herein, such as for example, the carrier apparatuses disclosed in U.S. Pat. No. 7,587,966. FIG. 5B2 shows the orientation of the chassis 102 on the carrier apparatus 308 while advancing in the machine direction. More particularly, FIG. 5B2 shows the chassis 102 with the lateral axis 126 of the chassis 102 generally parallel with the machine direction MD, and wherein the second longitudinal side edge 130 is the leading edge and the first longitudinal side edge 128 is the trailing edge.

As discussed below with reference to FIGS. 3, 5C, 5D, 5E, and 5F, the chassis 102 are transferred from the carrier apparatus 308 and combined with advancing, continuous lengths of substrates 406, 408, which may be referred to herein as belts, belt substrates, or elastic belt substrates. The substrates 406, 408 may be elastically extensible or inelastic. These substrates 406, 408 may be subsequently cut to form first and second belts 106, 108 on diapers 100, as illustrated in FIG. 1.

As illustrated in FIG. 4, the chassis 102 are transferred from the carrier apparatus 308 to a nip 316 between the carrier apparatus 308 and a roll 318 where the chassis 102 is combined with continuous lengths of advancing first substrate 406 and second substrate 408. The first substrate material 406 and the second substrate material 408 each define a wearer facing surface 312 and an opposing garment facing surface 314, as illustrated in FIG. 5C. The wearer facing surface 312 of the first substrate 406 may be combined with the garment facing surface 134 of the chassis 102 along the first waist region 116, and the wearer facing surface 312 of the second substrate 408 may be combined with the garment facing surface 134 of the chassis 102 along the second waist region 118. As shown in FIG. 4, adhesive 320 may be intermittently applied to the wearer facing surface 312 of the first and second substrates 406, 408 before combining with the discrete chassis 102 at the nip 316 between roll 318 and the carrier apparatus 308.

With reference to FIGS. 4 and 5D, a continuous length of absorbent articles 400 are defined by multiple discrete chassis 102 spaced from each other along the machine direction MD and connected with each other by the substrate assembly 190 which includes the second substrate 408 and the first substrate 406. As shown in FIG. 4, the continuous length of absorbent articles 400 advances from the nip 316 to a folding apparatus 500. At the folding apparatus 500, each chassis 102 is folded in the cross direction CD along a lateral axis 126 to place the first waist region 116, and specifically, the inner, body facing surface 132 into a facing, surface to surface orientation with the inner, body surface 132 of the second waist region 118. The folding of the chassis also positions the wearer facing surface 312 of the second substrate 408 extending between each chassis 102 in a facing relationship with the wearer facing surface 312 of the first substrate 406 extending between each chassis 102. As shown in FIGS. 4, 5D, and 5E, the folded discrete chassis 102 connected with the first and second substrates 406, 408 are advanced from the folding apparatus 500 to a bonder apparatus 200. The bonder apparatus 200 operates to bond, at least a portion of the region 336, which may include an overlap area 362, of the substrate assembly 190 thus creating discrete bond sites 336a. An overlap area 362 includes a portion of the second substrate 408 extending between each chassis 102 and a portion of the first substrate 406 extending between each chassis 102. As shown in FIGS. 4 and 5F, a continuous length of absorbent articles are advanced from the bonder apparatus 200 to a knife roll 338 where the regions 336 are cut into along the cross direction to create a first side seam 178 and a second side seam 180 on an absorbent article 100. It is to be appreciated that the regions 336 may be cut while the first and second substrates 406, 408 are disposed on the bonder apparatus 200. Thus, the first and second substrates 406, 408 may be joined and cut while being rotated by the bonder apparatus 200.

Although the absorbent article is described as having a substrate assembly that includes first and second substrates, it is to be appreciated that the absorbent article may have only one substrate or, alternatively, one or more substrates. For example, the substrate assembly may include a first substrate, a second substrate, a third substrate, and a fourth substrate. Further, it is to be appreciated that the chassis and substrate of the absorbent article may be one continuous substrate such that the overlap area is formed from the same substrate. As such, the bonder apparatus may operate to bond a continuous substrate at an overlap area to form one or more discrete bond sites.

Figure 6:
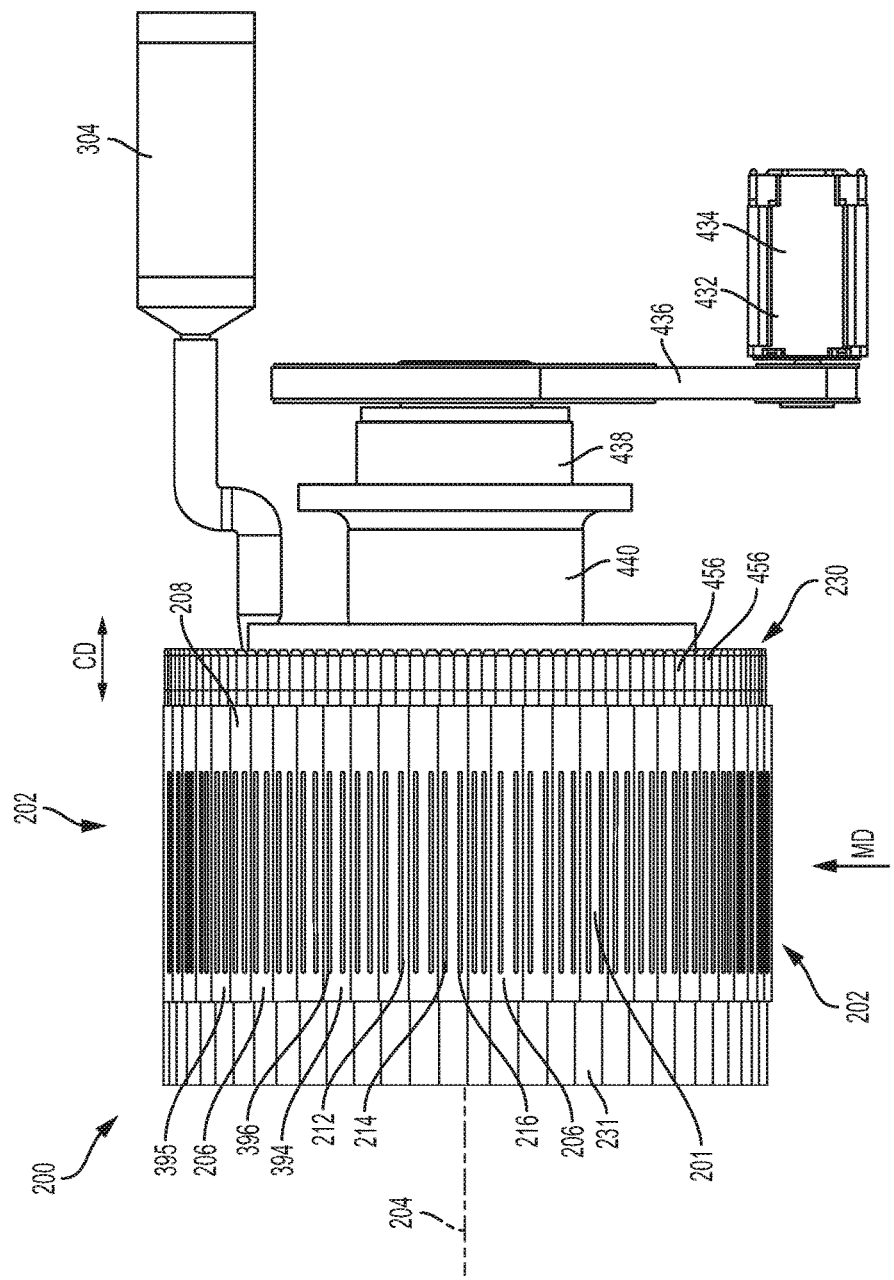
FIG. 6 is a side view of a bonder apparatus in accordance with one non-limiting embodiment of the present disclosure.

As previously discussed, the converting apparatus 300 may include a bonder apparatus 200. FIG. 6 illustrates a side view of an embodiment of a bonder apparatus 200 that may be used with the methods and apparatuses herein. As shown in FIG. 6, the bonder apparatus 200 may include a plurality of manifolds 202 rotatable about a central longitudinal axis of rotation 204. Each of the plurality of manifolds 202 may be disposed about the central longitudinal axis 204, such that the plurality of manifolds 202 substantially surround the central longitudinal axis 204 and form an outer circumferential surface 201. The bonder apparatus 200 may include at least 4 manifolds or at least ten manifolds, or at least twenty manifolds, or at least 40 manifolds, or at least 50 manifolds or greater. Each of the plurality of manifolds may be placed about the central longitudinal axis 204 such that adjacent manifolds are in abutting relationship or adjacent one another. Stated another way, there may be a gap between adjacent manifolds or the manifolds may abut one another.

Figure 10:
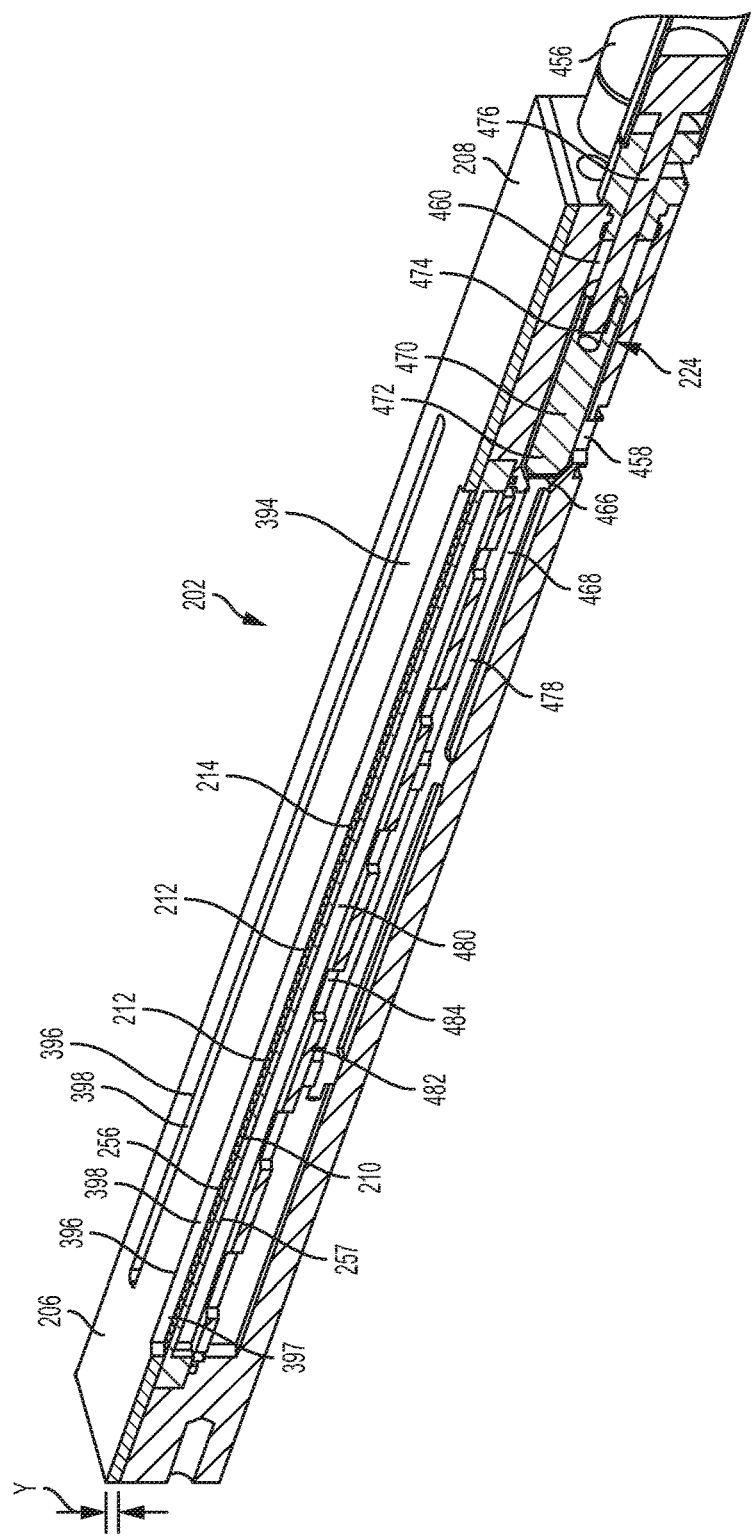
FIG. 10 is a partially cut-away perspective view of a manifold in accordance with one non-limiting embodiment of the present disclosure.

Each of the plurality of manifolds 202 includes a first end portion 206 and a second end portion 208, opposite the first end portion 206. Each of the plurality of manifolds may also include a support plate 394 that extends from the first end portion 206 to the second end portion 208 of the manifold 202, in a direction substantially parallel to the central longitudinal axis 204. The support plate 394 may include an external support surface 395 and an internal support surface 397, opposite the external support surface 395. The external support surface 395 of each of the support plates 394 forms at least a portion of the outer circumferential surface 201. The external support surface 395 of the support plate 394 may be configured to receive a portion of the substrate assembly 190. Further, the support plate 394 may define one or more slots 396 that extend vertically from the external support surface 395 to the internal support surface 397, as illustrated in FIG. 10. The one or more slots 396 may extend horizontally in a direction parallel to the central longitudinal axis 204. The internal support surface 397 of the support plate 394 may be in facing relationship with a nozzle plate 210, as will be discussed with reference to FIG. 10.

The nozzle plate 210 may define a plurality of apertures 212. The plurality of apertures 212 may extend in a direction substantially parallel to the central longitudinal axis 204 along the nozzle plate 210. In some embodiments, the plurality of apertures 212 may extend from the first end portion 206 to the second end portion 208 of the nozzle plate 210. However, it is to be appreciated that the plurality of apertures 212 may be any length and positioned in any configuration that is sufficient to heat the portion of the substrate assembly to be joined. As illustrated in FIG. 6, for example, the nozzle plate 210 may defines a first group of apertures 214 and a second group of apertures 216. The first group of apertures 214 may be adjacent the second group of apertures 216. The plurality of apertures 212 may be substantially surrounded by the one or more slots 396 defined by the support plate 394.

The bonder apparatus 200 may also include a plurality of support arms 231. Each support arm 231 may be joined to the first end portion 206 or the second end portion 208 of the manifold 202. The support arm 231 may be removably attached to the manifold 202, such as by screws, bots, or clamps. The support arm 231 may be used to extend the length of the outer circumferential surface 201 such that larger articles may be processed on a single bonder apparatus 200. The support arm 231 may be a substantially rigid member. The support arm 231 may also be used to protect the absorbent article from interfering with additional components of the bonder apparatus 200.

Still referring to FIG. 6, a heat member 304 may be positioned adjacent the plurality of manifolds 202. The heat member may be any device which increases in temperature by use of energy or radiation, such as an electric heater, an induction heater, which heats a thermally conductible object by electromagnetic induction, laser heating, ultrasonically heating. The heat member 304 may be used to heat the fluid. The fluid is heated to a temperature sufficient to at least partially melt at least a portion of the region 336 of the substrate assembly 190. The heated fluid is then passed to specific manifolds to be released through the plurality of apertures 212. It is to be appreciated that the fluid is heated to a temperature which accounts for any loss in temperature from being transferred from the heat member 304 to the manifold 202 and through the plurality of apertures 212.

The heated fluid may include ambient air or other gases. It is to be appreciated that the fluid may be heated to various temperatures and pressurized to various pressures. For example, in some embodiments, the fluid may be heated up to an exit temperature, or, stated another way, the temperature at which the fluid is released through the plurality of apertures, ranging from the lower melting point of first and second substrates minus 30° C. to the lower melting point of the first and second substrates plus 100° C. In some embodiments, the fluid pressure may range from $0.1 \times 10^5$ Newtons per square meter to $1 \times 10^6$ Newtons per square meter. In some embodiments, the heated fluid may be directed toward at least one of the first and second substrates for a time interval ranging from about 10 to about 1000 milliseconds or greater. Shorter or greater time intervals may be used.

The fluid may be sufficiently heated to enable at least a partial melting of at least a portion of the substrate assembly 190. A jet of the heated fluid may be directed toward the substrate assembly 190. The fluid may be allowed to penetrate the substrate assembly 190 such that at least a portion of each of the substrate layers is melted in the region, which may be an overlap area 362. The heated fluid, at a controlled temperature and pressure, may pass from the apertures, leading to the formation of controlled and concentrated jets of heated fluid, which are directed toward the region 336 of the substrate assembly 190 to be joined.

By controlled, it is meant that the temperature and pressure of the fluid are maintained within a specified range once the nominal set points are selected. For example, a set point may be selected and the temperature may then be maintained in a fixed range around the nominal set point, such as ±30° C., and the pressure may be maintained in a fixed range around the nominal set point, such as ±1 bar. The acceptable range will depend on the properties, such as softening point and/or melting temperature, of the materials to be joined and the nominal set point selected.

For example, a nominal set point above the melting temperature of one or more of the materials to be joined may require a tighter control range than a nominal set point well below the melting temperature of one or more materials to be joined. The control range may be asymmetrical about the nominal set point. By sufficiently heating, it is meant that the fluid is heated to a temperature that will enable at least partial melting, or at least softening, of the substrate or substrates. Sufficient heating may vary with the materials and equipment used. For example, if the heated fluid is applied to the substrate or substrates almost immediately, with little or no time to cool, the fluid may be heated to approximately the softening point or approximately the melting point of the substrate or substrates. If the heated fluid is directed to the substrate or substrates over some gap in time or distance, such that the heated fluid may cool somewhat before interacting with the substrate or substrates, it may be necessary to heat the fluid above, possibly significantly above, the softening point or melting point of the substrate or substrates.

The fluid may also be delivered with a pulsed application. The impact of the jet of heated fluid may be adjusted such that both the energy introduced by the jet plus the energy introduced by other means such as a heated anvil (if the anvil is heated), deformation of the substrate, and the internal friction of substrate layers are sufficient to at least partially melt the meltable components in the region 336 to create a certain tackiness, which will form a strong bond in the region 336, which may include an overlap area 362, upon compression. The melting of the meltable components may occur in a non-uniform manner throughout substrates in the region 336.

The duration of energy transfer in the process described herein may be a dynamic process, and may create a temperature gradient across the cross sections of the meltable components. That is, the core of the meltable components may remain solid while the exterior surface of the meltable components melt or come close to melting. Even below the melting temperature, the exterior surface may reach a softening point, such that plastic deformation of the material may occur at a much lower load than for the same material at ambient temperature. Thus, if one or more of the materials to be bonded have a softening point, the process may be adjusted to achieve a temperature in at least a portion of substrates between the softening point and the melting point. The use of a temperature at or above the softening point but below the melting point of one or more of the meltable components may allow for the creation of a strong bond between the substrate layers with reduced disruption to the structure of the meltable components e.g., attenuating or otherwise weakening the meltable components.

The release of the fluid may be controlled by a plurality of actuators 230 operatively engaged with a plurality of valves. Each of the plurality of manifolds 202 may be operatively engaged with at least one valve 224 and actuator 456. More specifically, in some embodiments, a single valve 224 may control the release of fluid to both the first group of apertures 214 and the second group of apertures 214 of a single manifold 202. In some embodiments, a first valve 224 may control the release of fluid through the first group of apertures 214 and a second valve 224 may control the release of fluid through the second group of apertures 216 of a single manifold 202.

A controller, not illustrated, may be operatively connected to each of the plurality of actuators 230. The controller is configured to pass instructions to the plurality of actuators, such that certain valves 224 change from a closed position, which prevents the flow of fluid, to an open configuration, which allows for the flow of fluid, or vice versa.

Figure 7:
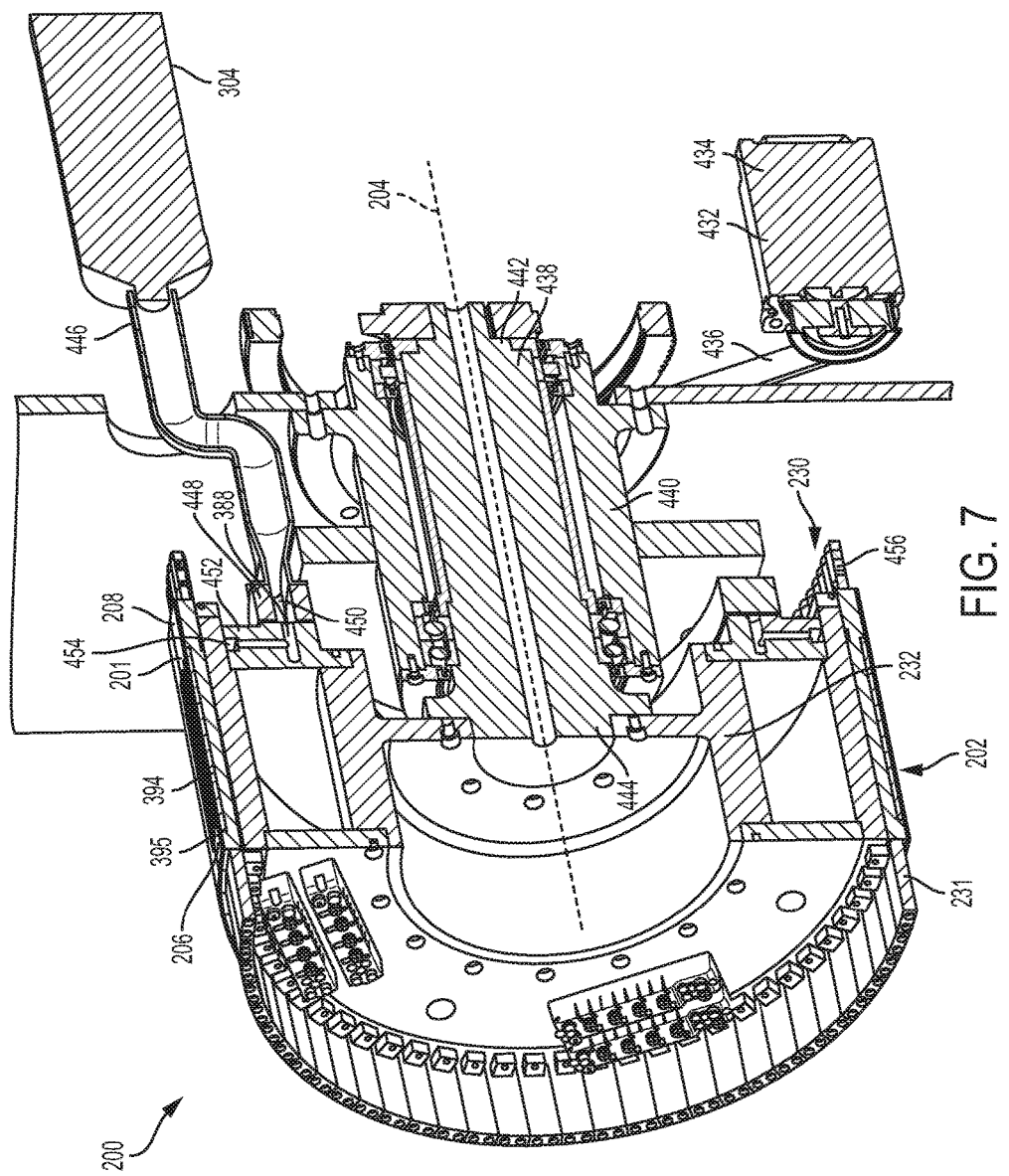
FIG. 7 is a partially cut-away perspective view of a bonder apparatus in accordance with one non-limiting embodiment of the present disclosure.

The bonder apparatus 200 may be driven by a drive member 432, such as a motor 434, as illustrated in FIGS. 6 and 7. The motor 434 may be any device that transmits rotational energy to the bonder apparatus. The motor 434 may be operatively linked or operatively engaged with the bonder apparatus using any technique known to those skilled in the art such as, for example, a gear to gear connection, transmission belting 436, and pulleys, gearboxes, direct couplings, and the like or any combination thereof.

The drive member 432 may be operatively engaged with a rotatable central shaft 438. The drive member 432 causes the rotatable central shaft 438 to rotate about the central longitudinal axis 204. The rotatable central shaft 438 includes a distal end portion 442 and a proximal end portion 444, opposite the distal end portion 442, as illustrated in FIG. 7. The drive member 432 may be operatively engaged with the distal end portion 442 of the rotatable central shaft 438.

The rotatable central shaft 438 may be rotatably connected to a stationary central shaft 440. The stationary central shaft 440 may substantially surround the rotatable central shaft 438. Stated another way, the rotatable central shaft 438 may extend through the stationary central shaft 440. In some embodiments, bearings, bushings, or other moveable connection may rotatably connect the rotatable central shaft 438 to the stationary central shaft 440, such that the rotatable central shaft 438 may rotate about the central longitudinal axis 204 as the stationary central shaft 440 remains fixed.

The proximal end portion 444 of the rotatable central shaft 438 may be connected to a support drum 232. The support drum 232 may extend about the central longitudinal axis 204 and be configured to rotate with the rotatable central shaft 438. The plurality of manifolds 202 may be disposed on the support drum 232. The plurality of manifolds 202 extend about the support drum 232 such that an outer circumferential surface 201 is formed. Thus, the support drum 232 and the plurality of manifolds rotate about the central longitudinal axis 204.

Figure 8:
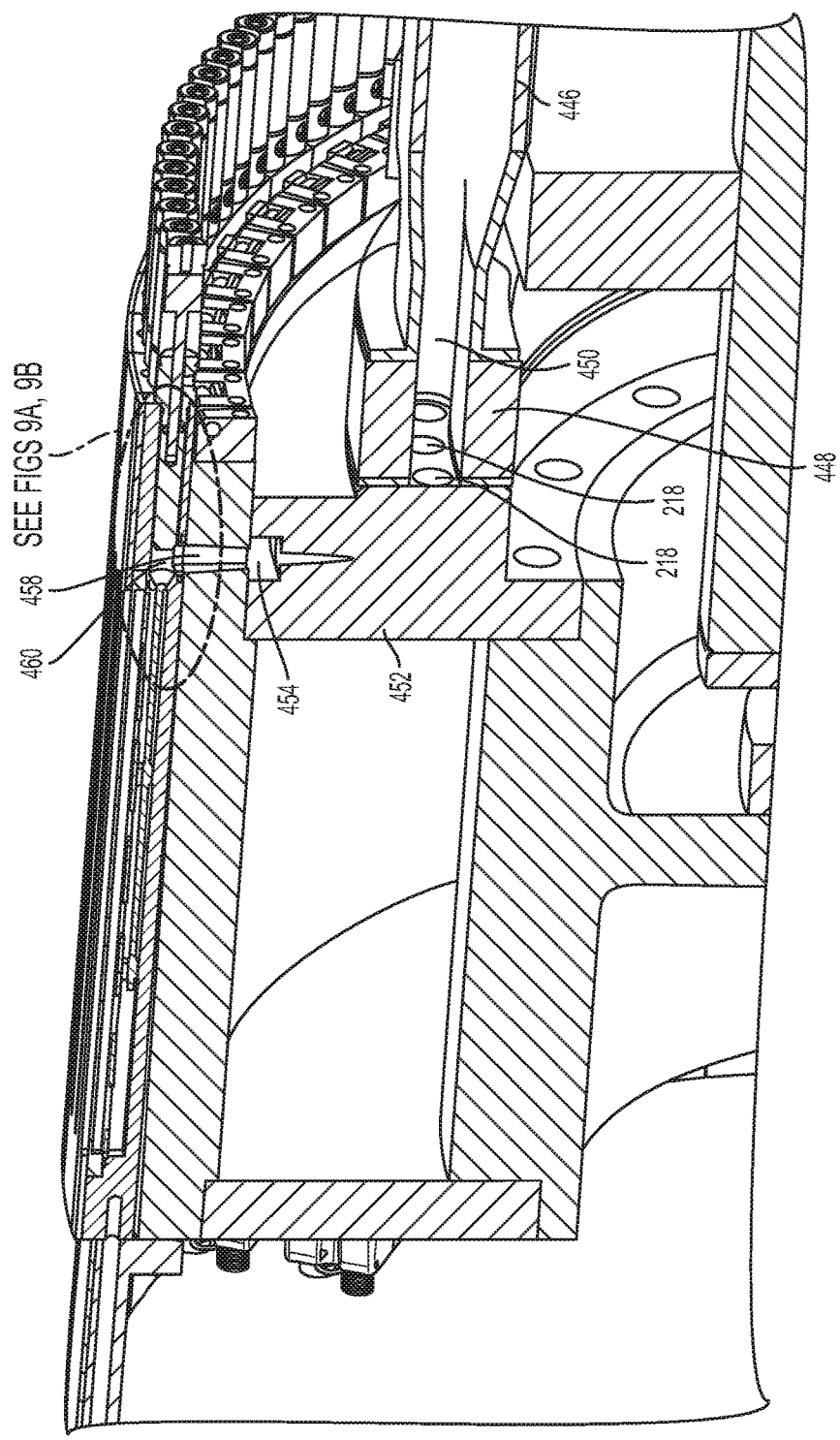
FIG. 8 is a partially cut-away perspective view of a portion of a bonder apparatus in accordance with one non-limiting embodiment of the present disclosure.

As previously discussed, the heat member 304 is configured to heat a fluid to a temperature sufficient to at least partially melt the substrate assembly. The heated fluid may then be transferred to the manifold 202. In some embodiments, the heated fluid may be transferred through tubing 446. The tubing 446 may be insulated to minimize heat loss as the fluid is being transferred. The tubing 446 may connect the heat member 304 to a cap member 448, as illustrated in FIGS. 7 and 8. The cap member 448 extends about the central longitudinal axis 204. The cap member 448 is operatively connected to the stationary central shaft 440. The cap member 448 defines an internal reservoir 450 that extends about a portion of the cap member 448. The internal reservoir allows fluid to pass from the tubing 446 to a fluid block 452.

It is to be appreciated that the bonder apparatus 200 may include more than one heat member 304. Each heat member 304 may be connected to tubing 446 which supplies the heated fluid to the cap member 448. The cap member 448 may include more than one internal reservoir 450. Thus, a single heat member may be fluidly connected, such as by tubing, to multiple internal reservoirs defined by the cap member 448. For example, the heat member may be fluidly connected to a first internal reservoir and a second internal reservoir, each defined by the cap member. Further, multiple heat members may be fluidly connected, such as by tubing, to each of the multiple internal reservoirs defined by the cap member 448. For example, a first heat member may be fluidly connected to a first internal reservoir defined by the cap member, and a second heat member may be fluidly connected to a second internal reservoir defined by the cap member.

The cap member 448 may be fluidly connected to a fluid block 452 as illustrated in FIGS. 7 and 8. The fluid block 452 may be configured to rotate about the central longitudinal axis 204. The fluid block 452 may define a plurality of fluid inlets 218. Thus, as the fluid block rotates about the central longitudinal axis 204, the plurality of fluid inlets 218 move such that they are in fluid connection with the internal reservoir 450 of the cap member 448. Fluid may be transferred from the internal reservoir 450 to a portion of the plurality of fluid inlets 218 as the portion of the plurality of fluid inlets 218 rotates by the one or more internal reservoirs 450. The fluid inlets 218 may be any shape, such as circular, oval, rectangular, that allows fluid to move from the internal reservoir through the fluid inlet 218. It is also to be appreciated that the fluid inlet 218 may be an inlet groove that extends about the fluid block 452. Thus, the inlet groove may extend about the central longitudinal axis 204 or a portion thereof.

The fluid inlets 218 allow the fluid to transfer into a fluid pathway 388, as illustrated in FIG. 7. The fluid may travel through the fluid pathway 388 and exit through a fluid outlet 454, as illustrated in FIG. 8. The fluid may be transferred from the fluid outlet 454 to a fluid opening 458 defined by the manifold 202, as illustrated in FIGS. 8, 9A, and 9B. The fluid opening 458 may be any shape that allows fluid to move from the fluid outlet 454 to the manifold 202. For example, the fluid opening 458 may be circular, oval, square, or rectangular in cross section. The fluid opening 458 may be fluidly connected to a control chamber 460 defined by the manifold 202. The control chamber 460 extends from the fluid opening 458 to the second end portion 208 of the manifold 202. The control chamber 460 may extend through the end portion 462 of the manifold 202 forming a first control chamber opening 464, as illustrated in FIGS. 9A and 9B. The control chamber opening 464 may be configured to receive an engagement member 470. Opposite the control chamber opening 464 is a second control chamber opening 466. The second control chamber opening 466 may be fluidly connected to a fluid chamber 468 defined by the manifold 202.

The control chamber 460 may be configured to receive an engagement member 470, and the engagement member 470 may be slidably engaged with the control chamber 460. The control chamber 460 and the engagement member 470 form a valve 224. The engagement member 470 may be an elongated member having substantially the same shape as the control chamber 460. For example, the engagement member 470 may have a circular or oval cross-section. The engagement member 470 may have a proximal end portion 472 adjacent the fluid chamber 468 and a distal end portion 474, opposite the proximal end portion 472 and adjacent the second end portion 208 of the manifold 202. The engagement member 470 may be slidably engaged with the control chamber 460. More specifically, as illustrated in FIG. 9B, the engagement member 470 may slide into a first configuration. In the first configuration, a portion of the engagement member 470 may be positioned over the fluid inlet and/or the proximal end portion 472 may abut the area of the control chamber 460 adjacent the second control chamber opening 466 such that fluid is prevented from entering the fluid chamber 468. Further, as illustrated in FIG. 9A, the engagement member 470 may slide into a second configuration. In the second configuration, the engagement member 470 may be positioned adjacent the fluid opening 458 and/or the proximal end portion 472 of the engagement member 470 may be spaced from the second control chamber opening 466 such that fluid may flow into the fluid chamber 468. In the second configuration, fluid may be transferred through the fluid opening 458 into the control chamber 460 and through the second control chamber opening 466 of the control chamber 460 into the fluid chamber 468.

Still referring to FIGS. 9A and 9B, the distal end portion 474 of the engagement member 470 may be operatively connected to an actuator 456. More specifically, the actuator 456 may include a plunger member 476. The plunger member 476 may extend through the first control chamber opening 464 defined by the end portion 462 of the manifold 202. A portion of the plunger member 476 may engage the distal end portion 474 of the engagement member 470. The plunger member 476 of the actuator 456 may be driven by mechanical, electrical, hydraulic, pneumatic, or some other energy source, such that the plunger member 476 causes the engagement member 470 to slide from the first configuration to the second configuration. The plunger member 476 is connected to the engagement member 470 such that the plunger member 476 and the engagement member 470 move together. For example, when the plunger member 476 is caused to move in a direction toward the second control chamber opening 466, the engagement member 470 moves in the same direction.

As previously stated, when the engagement member 470 slides to a second position such that the engagement member 470 may be spaced from the second control member opening 466 and/or adjacent the fluid opening 458, fluid may transfer through the fluid opening 458 into the control chamber 460 and through the second control chamber opening 466 into the fluid chamber 468. As illustrated in FIG. 10, the fluid chamber 468 may be separated into a first fluid chamber 478 and a second fluid chamber 480. The first fluid chamber 478 may be separated from the second fluid chamber 480 by a notched plate 482 defining one or more notched openings 484. The notched plate 482 aids in the distribution of fluid throughout the manifold 202. More specifically, the notched plate 482 includes notched opening 484. The notched openings 484 may be a various sizes. The notched openings 484 control the flow of fluid by regulating the amount of fluid that passes through the notched openings 484 as the fluid is transferred through the fluid chamber 468 toward the first end portion 206 of the manifold 202.

It is to be appreciated that the fluid chamber 468 may be separated into any number of sections. It is also to be appreciated that the fluid chamber 468 may be a single chamber that is not separated.

Still referring to FIG. 10, a nozzle plate 210 may be postponed adjacent the fluid chamber 468. For example, the nozzle plate 210 may extend along the length of the fluid chamber 468. Stated another way, the nozzle plate 210 may extend from the first end portion 206 of the manifold 202 to the second end portion 208 of the manifold 202. The nozzle plate 210 includes a first nozzle plate surface 256 and second nozzle plate surface 257. The second nozzle plate surface 257 may be in facing relationship with the fluid chamber 468. The nozzle plate 210 may define a plurality of apertures 212 that extend through the nozzle plate from the first nozzle plate surface 256 to the second nozzle plate surface 257. The fluid may be transferred from the fluid chamber 468 through the plurality of apertures 212. The plurality of apertures 212 may be arranged into a first group of apertures 214 and a second group of apertures 216. The groups of apertures may be arranged with respect to one another in any configuration that at least partially melts the substrate assembly in the desired area. The apertures 212 may be any shape sufficient to transfer fluid to the desired area of the substrate assembly. For example, each apertures may have a circular cross-section, an oval cross-section, a rectangular cross-section, or the like.

The manifold 202 may also include a support plate 394, as illustrated in FIG. 10. The support plate 394 may be disposed on the first, external nozzle plate surface 256. The support plate 394 may cover a portion of the nozzle plate 210. The support plate 394 may include one or more slots 396. Each of the slots 396 may substantially surround the plurality of apertures 212 or a portion of the plurality of apertures 212. Each slot may include one or more slot walls 398 that extend from the first nozzle plate surface 256 to the external surface of the support plate or the outer circumferential surface 201 and substantially surround a portion of one or more apertures 212. The support plate 394 may include a thickness Y of from about 0.5 millimeters to about 20 millimeters, including all 0.1 increments therebetween. The support plate 394 may be any thickness Y such that the substrate assembly 190 is a desired distance from the external, first nozzle plate surface 256 and, thus, the plurality of apertures 212. For example, the thickness Y may be such that the such that the distance from the layer of the substrate assembly positioned closest to the apertures and the first nozzle plate surface 256 may range from 0.5 millimeters to about 20 millimeters, or between about 0.5 millimeters and about 5 millimeters, or between about 0.5 millimeters and about 3 millimeters, including all 0.1 millimeter increments between the recited ranges. Control of the distance between the substrate assembly 190 and the apertures 212 may also result in a relatively more predictable fluid spray and melt pattern during the fluid application and heating/melting process. It is also to be appreciated that the manifold 202 may not include a support plate 394 and the substrate assembly 190 may be disposed on the first nozzle plate surface 256. Thus, the substrate assembly 190 may abut the external surface of the nozzle plate and the apertures of the nozzle plate. Thus, the distance between the substrate assembly 190 and the external surface 256 may be about zero millimeters.

It is to be appreciated that the manifold may include temperature sensors such that the temperature of the fluid chamber 386, the fluid supplied to the plurality of apertures, and the fluid released through the plurality of apertures can be monitored. The temperature of the heat member 304 may be changed based on the output from the temperature sensors.

Figure 11A:
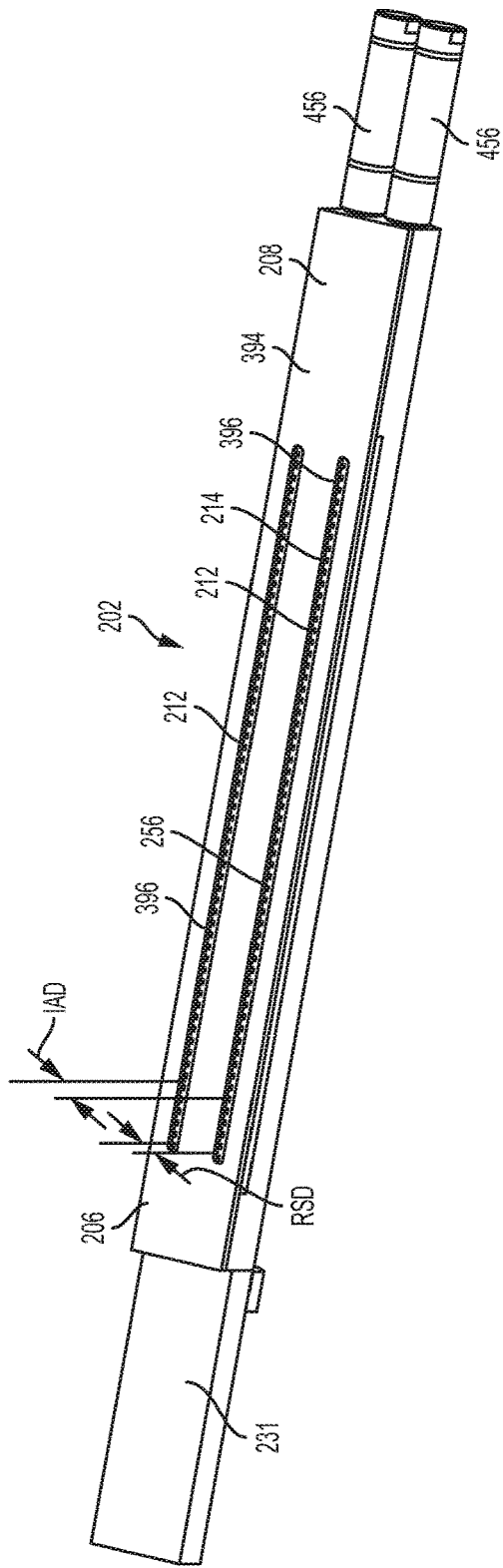
FIG. 11A is a perspective view of a manifold operatively connected to actuators in accordance with one non-limiting embodiment of the present disclosure.
Figure 11C:
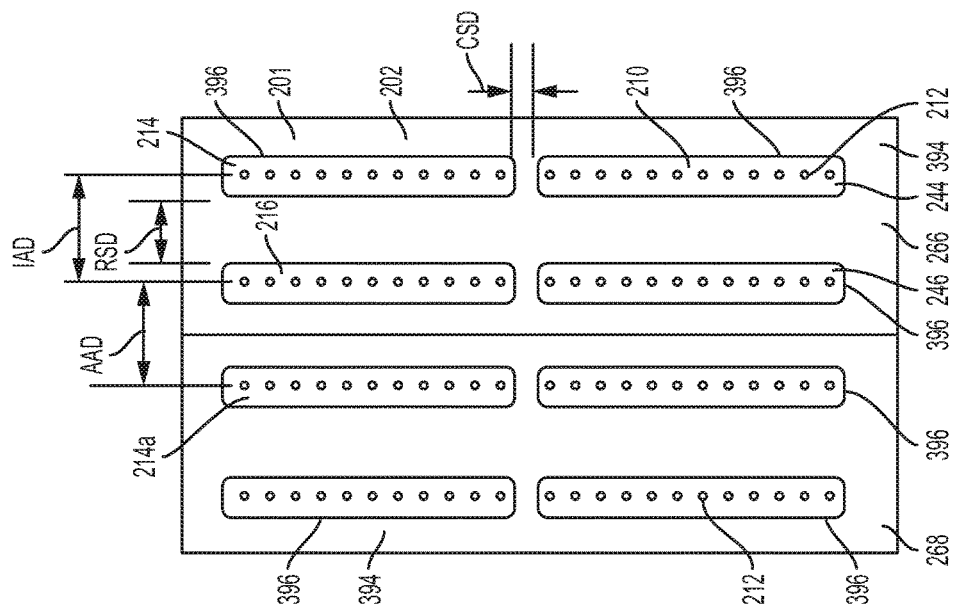
FIG. 11C is a top view of a portion of two manifolds in accordance with one non-limiting embodiment of the present disclosure.
Figure 11B:
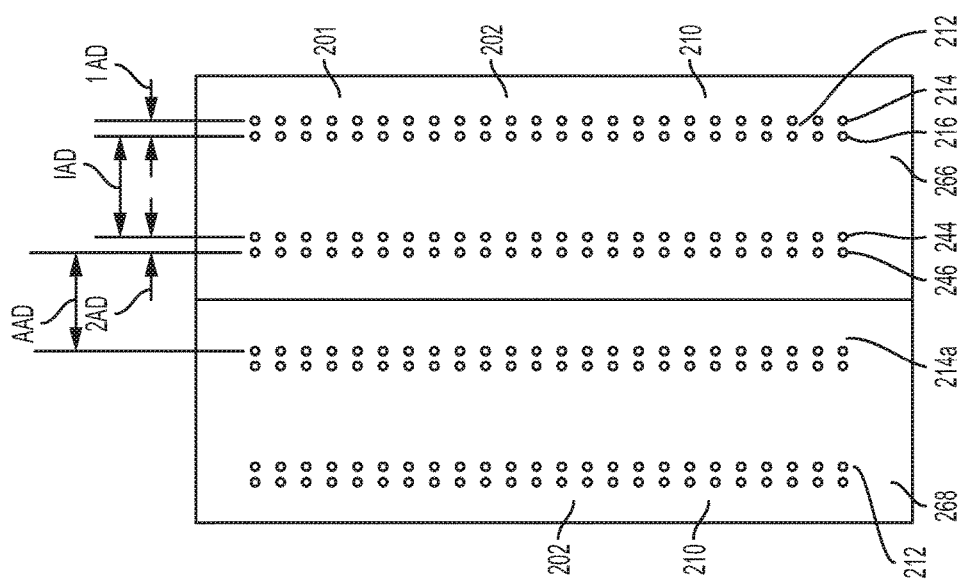
FIG. 11B is a top view of a portion of two manifolds in accordance with one non-limiting embodiment of the present disclosure.

As illustrated in FIGS. 11A-11C, the one or more slots 396 may be separated by a radial slot distance RSD. The radial slot distance RSD is the distance measured along the outer circumferential surface 201 in the machine direction MD between a first plane taken parallel to the central longitudinal axis 204 and intersecting the point or portion of the first slot that is nearest to the adjacent slot in the machine direction and a second plane taken parallel to the central longitudinal axis 204 and intersecting the point or portion of the adjacent slot that is nearest to the first slot in the machine direction. The RSD may be from about 5 millimeters to about 80 millimeters and/or from about 15 millimeters to about 40 millimeters, including all 0.1 millimeters therebetween, such as 8.5 millimeters. The one or more slots 396 may also be separated by a cross direction slot distance CSD, as illustrated in FIG. 11C. The cross direction slot distance CSD is the distance measured along the outer circumferential surface 201 in the cross direction CD, which is parallel to the central longitudinal axis 204, between a first plane taken perpendicular to the central longitudinal axis 204 and intersecting the point or portion of the first slot that is nearest to the adjacent slot in the cross direction CD and a second plane taken perpendicular to the central longitudinal axis 204 and intersecting the point or portion of the adjacent slot that is nearest to the first slot in the cross direction. The cross direction slot distance CSD may be from about 3 mm to about 10 mm and/or from about 5 mm to about 25 mm and/or from about 30 mm to about 100 mm and/or from about 50 mm to about 500 mm, including all 0.1 mm therebetween.

As previously discussed, the nozzle plate 210 may include a plurality of apertures 212. The plurality of apertures 212 may be arranged into a first group of apertures 214 and a second group of apertures 216. The first and second group of apertures 214, 216 may extend from the first end portion 206 to the second end portion 208 of a first manifold 202. In some embodiments, the plurality of apertures 212 may also include a third group of apertures 244 and a fourth group of apertures 246, as illustrated in FIG. 11B. The third and fourth group of apertures 244, 246 may also extend from the first end portion 206 to the second end portion 208 of the first manifold 202, 266. Further each of the groups of apertures may be substantially parallel to one another. It is to be appreciated that the plurality of apertures may be arranged in any configuration which corresponds to the area of the substrate assembly to be at least partially melted. For example, one or more rows of apertures may be used or a random arrangement of apertures may be used.

The first group of apertures 214 and the second group of apertures 216 may be separated by a first aperture distance 1AD. The first aperture distance 1AD may be from about 1 mm to about 15 mm and/or from about 2 mm to about 8 mm and/or from about 2.5 mm to about 5 mm, including all 0.1 mm between the recited ranges. Similarly, the third group of apertures 244 and the fourth group of apertures 246 may be separated by a second aperture distance 2AD. The second aperture distance 2AD may be greater than, less than, or equal to the first aperture distance 1AD. The second aperture distance 2AD may be from about 1 mm to about 20 mm, including all 0.1 mm between the recited range. Further, the second group of apertures 216 may be separated from the third group of apertures 244 by an intermediate aperture distance IAD. The intermediate aperture distance IAD may be long enough such that additional processes may be performed on the substrate, such as cutting or scoring. The intermediate aperture distance IAD may be from about 5 mm to about 20 mm and/or from about 4 mm to about 40 mm, including all 0.1 mm between the recited ranges.

Further still, the fourth group of apertures 246, as illustrated in FIG. 11B, or the group of apertures closest to the adjacent manifold may be separated by the first group of apertures 214a disposed on an adjacent or a second manifold 202, 268 by an adjacent aperture distance AAD. The adjacent aperture distance AAD may be from about 5 mm to about 40 mm and/or from about 15 mm to about 80 mm and/or from about 20 mm to about 200 mm, including all 0.1 mm between the recited ranges. The aforementioned distances between each of the groups of apertures may be measured along the outer circumferential surface 201 in a direction parallel to the machine direction MD of the bonder apparatus 200. Further, the distances are measured from the center of the aperture. It is to be appreciated that each manifold may be configured to have the same pattern of apertures. Thus, the distance between groups of apertures on a given manifold may be about the same as the distance between the groups of apertures on another manifold.

Referring to FIG. 11C, the bonder apparatus 200 may include a plurality of support plates 394. A support plate 394 may be disposed on each of the plurality of nozzle plates 210 and may be used to separate the substrate assembly from the nozzle plate by a predetermined distance. Each of the support plates 294 may define one or more slots 396. The slots 396 may be positioned to substantially surround the plurality of apertures 212. For example, as illustrated in FIG. 11C, the support plate 294 includes four slots 396. A first slot 396 surrounds the first group of apertures 214 and a second slot 396 surrounds the second group of apertures 216. It is to be appreciated that a single slot may surround more than one group of apertures. Similar to the above, the first group of apertures 214 may be separated from the second group of apertures 216 by an intermediate aperture distance IAD. Further, the second group of apertures 216 of the first manifold 202, 266 may be separated from a first group of apertures 214a on the adjacent or second manifold 202, 268 by an adjacent aperture distance AAD. Further still, as previously discussed, the slots 396 defined by the support plate 394 disposed on the first manifold 202, 266 may be separated by a radial slot distance RSD and a cross direction slot distance CSD. It is to be appreciated that the support plate 294 may define more than one slot 396. These slots 396 may be separated from adjacent slots in both the machine direction MD and the cross direction CD, as illustrated in FIG. 11C. It is to be appreciated that the slots may be any shape and any size such that a group of apertures is substantially surrounded and the substrate assembly is adequately supported.

As previously discussed, fluid may be released through the plurality of apertures 212. The release of fluid through the plurality of apertures 212 may be controlled by the valves 224, as illustrated in FIGS. 9A and 9B. More specifically, one or more of the plurality of valves may be controlled such that any combination of the groups of apertures may release the fluid. For example, one or more values may configured to be positioned in an open position, which positions the engagement member in the second configuration, such that fluid is released through the first group of apertures 214 and the third group of apertures 244 and no fluid is released through the second group of apertures 216 and the fourth group of apertures 246, as illustrated in FIGS. 11B and 11C. In another example, the first and second group of apertures 214, 216 may be configured to release fluid and the third and fourth group of apertures 244, 246 may not release fluid. In yet another example, the second group of apertures 216 and the fourth group of apertures 246 may be configured to release fluid and the first and third group of apertures 214, 244 may not release fluid. In yet another example, the first, second, third, and fourth groups of apertures 214, 216, 244, and 246 may be configured to release the fluid. The dimensions and characteristics of the substrate assembly to be at least partially melted may be used to determine which one of the groups of the plurality of apertures releases fluid. Thus, the configuration of which of the plurality of apertures release fluid may change as the bonder apparatus 200 traverses about the central longitudinal axis 204. As illustrated in FIG. 11A, the manifold may be configured to operatively connect to one or more actuators 456. The number of actuators 456 operatively connected to a single manifold may be determined based on how the apertures are intended to be controlled. The actuator 456 may be any device that can be configured to be in a first position or a second position based on input from a controller. The actuator 456 operatively engages the valve 230, which may be configured to control one control chamber or more than one control chamber.

A controller, not illustrated, may be operatively connected to each of the plurality of actuators 230. The controller is configured to pass instructions to the plurality of actuators, such that certain valves 224 change from an open position to a closed position or vice versa.

Figure 12:
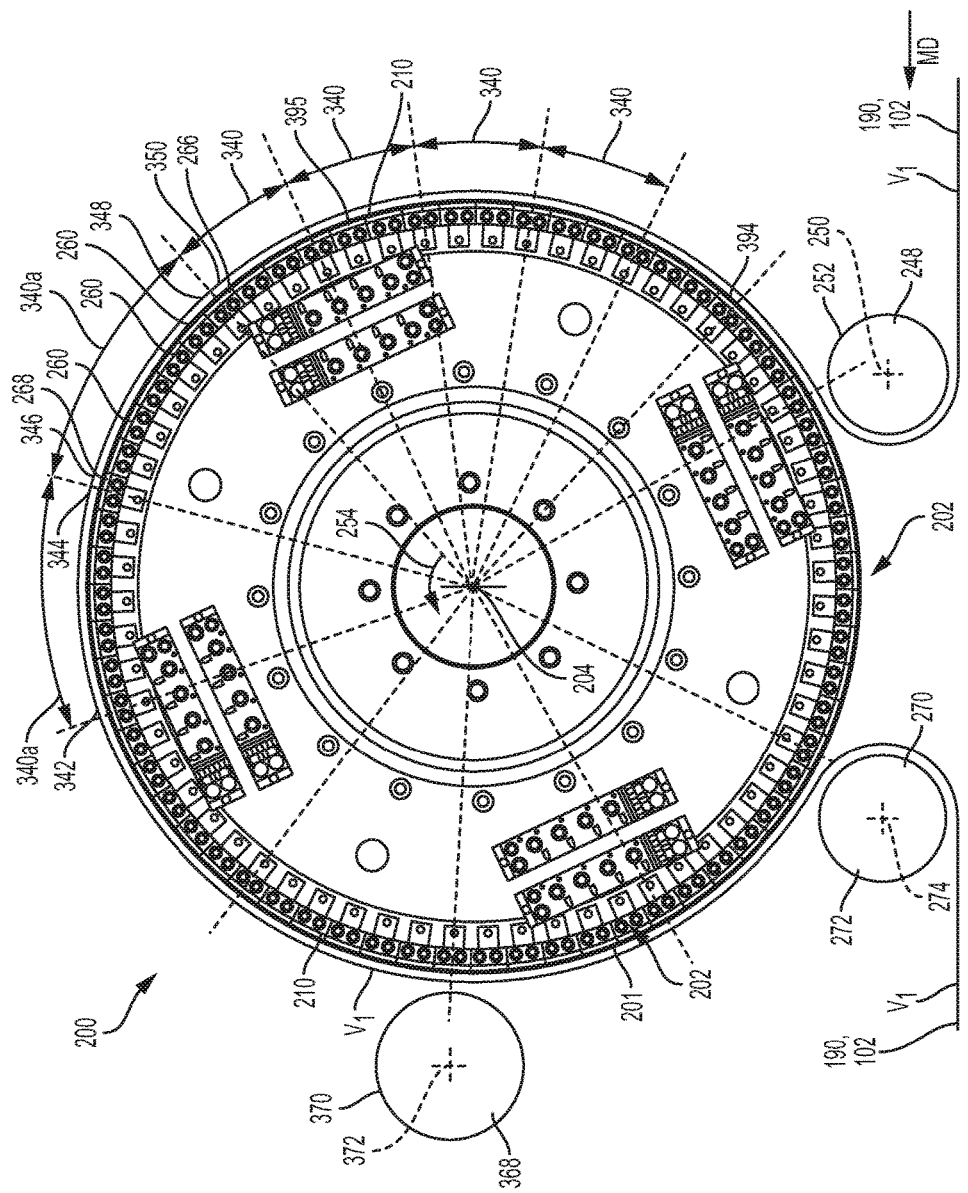
FIG. 12 is an end view of a bonder apparatus in accordance with one non-limiting embodiment of the present disclosure.
Figure 13A:
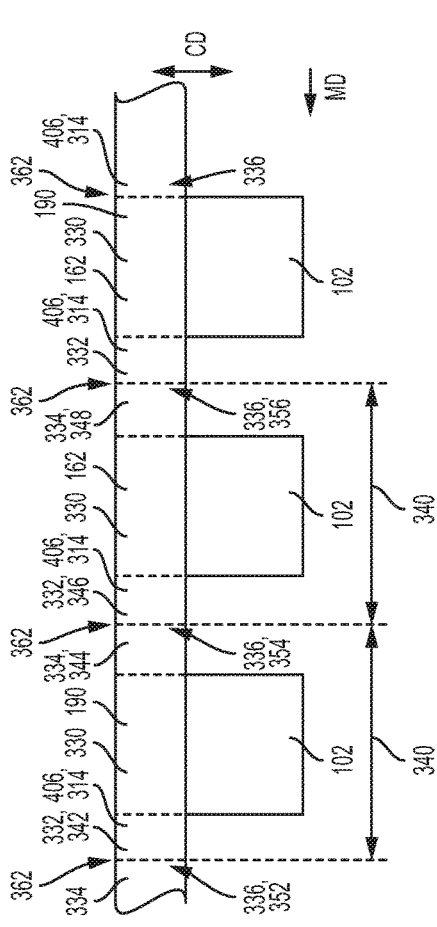
FIG. 13A is a top view of multiple discrete chassis attached to a first elastic belt substrate and a second elastic belt substrate in accordance with one non-limiting embodiment of the present disclosure.
Figure 13B:
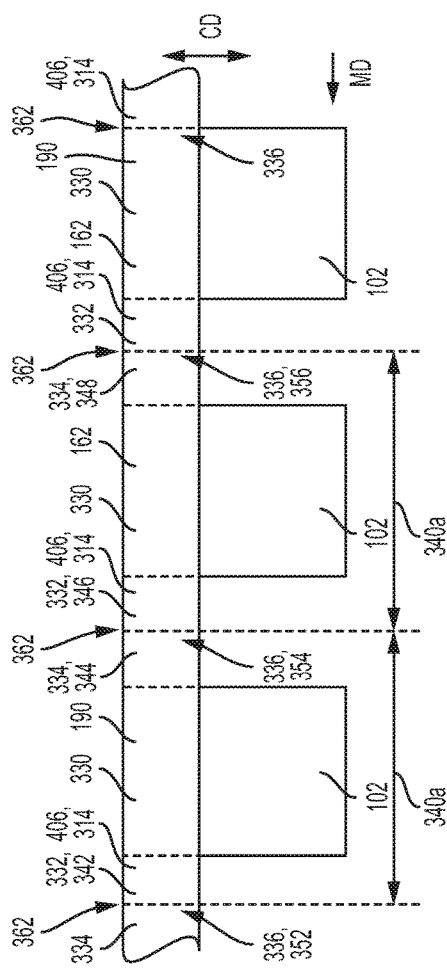
FIG. 13B is a top view of multiple discrete chassis attached to a first elastic belt substrate and a second elastic belt substrate in accordance with one non-limiting embodiment of the present disclosure.

Referring to FIGS. 12, 13A, and 13B, the substrate assembly 190, which may include the folded chassis 102, may advance in the machine direction MD to the bonder apparatus 200. As previously discussed, a substrate assembly 190 may include a first substrate and a second substrate in a facing relationship. It is to be appreciated that a substrate assembly 190 may include any number of substrates in any partially overlapping configuration. For example, the substrate assembly 190 may include a single folded substrate. As previously described, the first substrate and the second substrate may be used to form a first belt and a second belt of the absorbent article. The first substrate and the second substrate may be elastically extensible in at least one of the machine direction MD and the cross direction CD. The first and second substrates may include regions 336 intermittently spaced along the machine direction MD, wherein each region 336 may include a leading portion 332 and a trailing portion 334. For example, as illustrated in FIG. 13A, a first region 352 may include a first leading portion 342 and a subsequent or adjacent region in the machine direction MD, such as a second region 354, may include a first trailing portion 344 and a second leading portion 346 and yet another subsequent or adjacent region in the machine direction MD, such as a third region 356, may include a second trailing portion 348.

Each leading portion and trailing portion may define a process product pitch 340, 340a. More specifically, for example, a process product pitch 340, 340a refers to the distance measured parallel to the machine direction MD between the area at which a leading edge portion and a trailing edge portion meet in a first region to the area at which a leading edge portion and a trailing edge portion in a subsequent, adjacent region meet, as illustrated in FIGS. 13A and 13B. The length of the process product pitch may change based on the size of the absorbent article, the amount of elasticity of the substrate assembly, and the process tension placed on the substrate assembly as the substrate assembly is advanced in the machine direction MD. It is to be appreciated that the process product pitch includes the process tension placed on the substrate during processing.

As previously stated, absorbent articles come in a variety of sizes. For example, one absorbent article may include a larger chassis and a larger belt as compared to another absorbent article that may include a smaller chassis and a smaller belt, as illustrated in FIGS. 13B and 13A, respectively. Thus, the plurality of manifolds 202 may be used such that the absorbent article including the larger chassis and the larger belt can be manufactured on the same equipment as the absorbent article including the smaller chassis and the smaller belt. This prevents manufacturers from having to switch out equipment or to make large modifications to the equipment for manufacturing different sized articles, which is both costly and time consuming.

For example, the same bonder apparatus 200 may be used to process the substrate assembly illustrated in 13A and the substrate assembly illustrated in FIG. 13B. As shown, the substrate assembly of FIG. 13A has a shorter process product pitch 340 than the process product pitch 340a of the substrate assembly of FIG. 13B. Due to the number of manifolds and the spacing of the groups of apertures, a number of different sized absorbent articles may be manufactured on a single bonder apparatus 200. However, the bonder apparatus 200 may be designed for a minimum product pitch based on the diameter of the bonder apparatus 200, the number of manifolds 202, and the distance between apertures 212.

As illustrated in FIG. 12, the substrate assembly 190 may advance in the machine direction MD toward the bonder apparatus 200 at a first velocity $V_1$. Further, the substrate assembly 190 may be held at a process tension as the substrate assembly is advanced toward the bonder apparatus 200. A guide roll 248 configured to rotate about a first axis of rotation 250 and including a first outer circumferential surface 252 may be used to transfer the substrate assembly 190 onto the bonder apparatus 200. The substrate assembly 190 may be disposed on a portion of the outer circumferential surface 252 of the guide roll 232 as the substrate assembly is transferred to the bonder apparatus 200.

The bonder apparatus 200 includes a plurality of manifolds 202 that may be configured to rotate about an axis of rotation 204 in a direction indicated by arrow 254. Each of the plurality of manifolds 202 includes a nozzle plate 210. The nozzle plate 210 may include a first, external surface 256. The first, external surface 256 of the nozzle plate 210 may be configured to receive the substrate assembly 190 and/or the folded chassis 102. More specifically, as the substrate assembly 190 advances onto the bonder apparatus 200, the substrate assembly 190 is received by the nozzle plate 210 of each manifold 202, which forms the outer circumferential surface 201 of the bonder apparatus 200. It is also to be appreciated that, in some embodiments, a support plate 394 may be disposed on the nozzle plate 210, and the support plate 394 may be configured to receive the substrate assembly and form the outer circumferential surface 201.

Figure 13C:
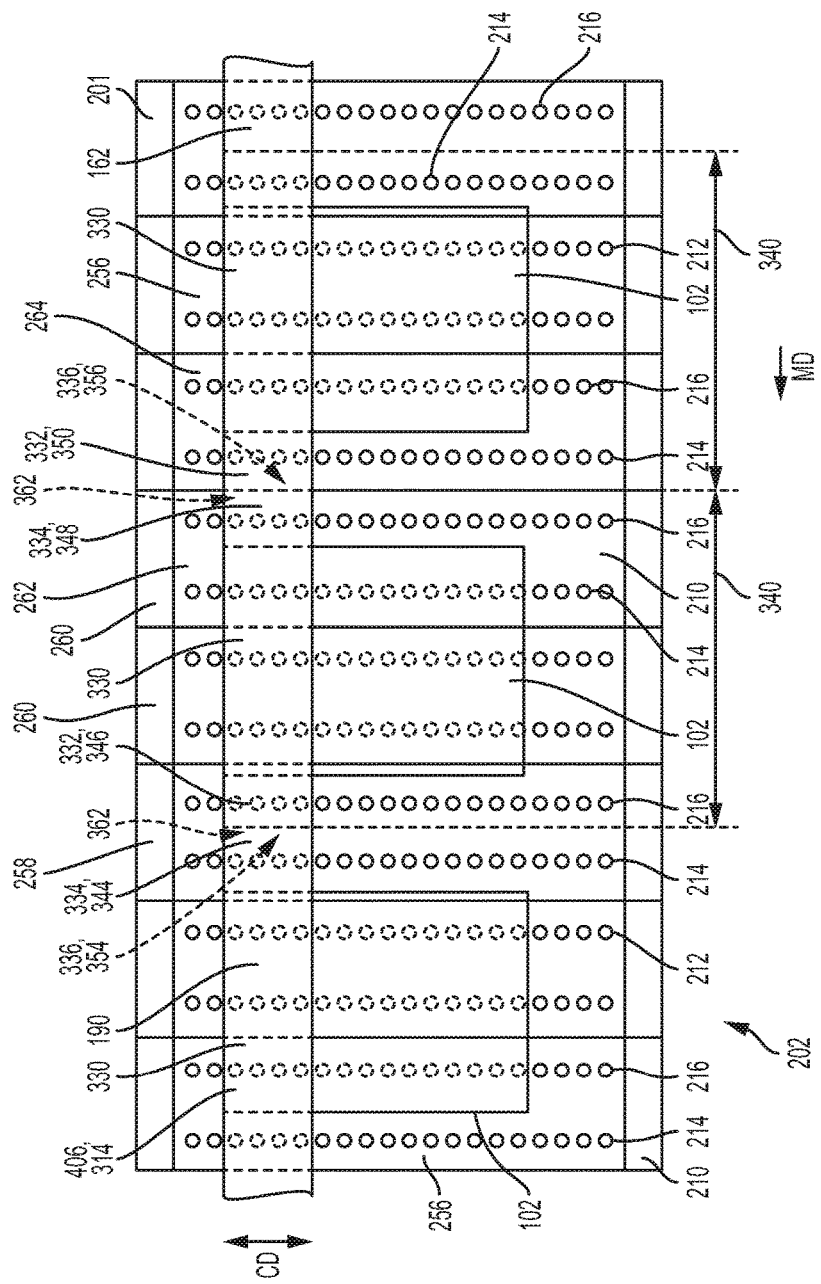
FIG. 13C is a top view of a portion of multiple discrete chassis attached to a first elastic belt substrate and a second elastic belt substrate disposed on a portion of the bonder apparatus in accordance with one non-limiting embodiment of the present disclosure.
Figure 13D:
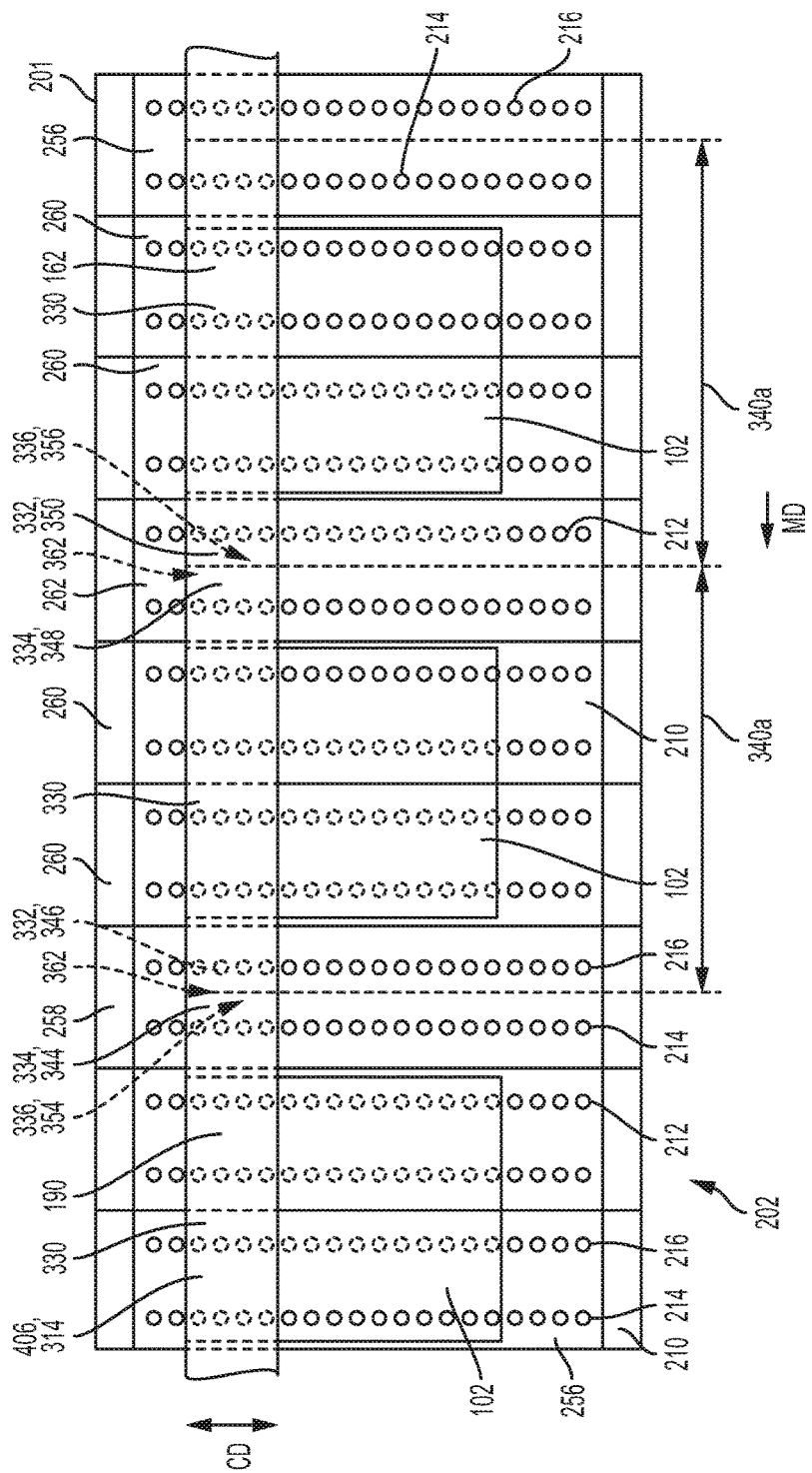
FIG. 13D is a top view of a portion of multiple discrete chassis attached to a first elastic belt substrate and a second elastic belt substrate disposed on a portion of the bonder apparatus in accordance with one non-limiting embodiment of the present disclosure.

As illustrated in FIGS. 13C and 13D, the substrate assembly 190 may be positioned on the first nozzle plate surface 256 such that the areas of the substrate assembly to be bonded are disposed on a portion of the group of apertures 214, 216. For example, as illustrated in FIG. 13C, the second region 354 of the substrate assembly 190 may be disposed on a first nozzle plate 258. More specifically, the first trialing portion 344 may be disposed on a portion of a first group of apertures 214 defined by the first nozzle plate 258 and the second leading portion 346 may be disposed on a portion of a second group of apertures 216 defined by the first nozzle plate 258. The central portion 330 of the substrate assembly 190 between the second leading portion 346 and the subsequent second trailing portion 348, extending in a direction parallel to the machine direction MD, may extend across intermediate manifolds 260 or portions thereof. The chassis 102 may also be disposed on the intermediate manifolds 260. Following the central portion 330 of the substrate assembly 190 disposed on the intermediate manifolds 260, the second trailing portion 348 may be disposed on a portion of a second nozzle plate 262 and the third leading portion 250 may be disposed on a third nozzle plate 264. More specifically, the second trailing portion 348 may be disposed on a second group of apertures 216 of the second nozzle plate 262 and a third leading portion 350 may be disposed on a portion of a first group of apertures 214 of the third nozzle plate 264. The substrate assembly 190 may be positioned such that the leading portion and the trailing portion are each disposed on an adjacent group of apertures. It is to be appreciated that adjacent groups of apertures do not have to be defined by the same nozzle plate. As will be discussed in more detail herein, fluid is released through the groups of apertures on which the leading edge portion and the trailing edge portion of the substrate assembly are disposed.

In another example, as illustrated in FIG. 13D, when the substrate assembly 190 is disposed on the outer circumferential surface 201 of the bonder apparatus, the second region 354 of the substrate assembly 190 may be disposed on a first nozzle plate 258. More specifically, the first trailing portion 344 may be disposed on a portion of a first group of apertures 214 of the first nozzle plate 258 and the second leading portion 346 may be disposed on a portion of a second group of apertures 216 of the first nozzle plate 258. The central portion 330 of the substrate assembly 190 between the second leading portion 346 and the subsequent second trailing portion 346, extending in a direction parallel to the machine direction MD, may extend across intermediate manifolds 260 or portions thereof. The chassis 102 may also be disposed one or more of the intermediate manifolds 260. Following the central portion 330 of the substrate assembly 190 disposed on the intermediate manifolds 260, a region 336 of the substrate assembly 190 may be disposed on a second nozzle plate 262. The second trailing portion 348 may be disposed on a portion of a first group of apertures 214 defined by the second nozzle plate 262 and a third leading portion 350 may be disposed on a portion of a second group of apertures 216 defined by the second nozzle plate 262. As illustrated in FIGS. 13C and 13D, the process tension, the process product pitch 340, 340a, and the distance between the groups of apertures are all factors in aligning the leading edge portion and the trailing edge portion of the substrate assembly with the apertures defined by the nozzle plates.

As illustrated in FIG. 12, the substrate assembly 190 rotates with the plurality of manifolds 202 about the central longitudinal axis 204 of rotation. The substrate assembly 190 may have the same process product pitch or different process product pitches along the length of the substrate assembly 190, which is parallel with the machine direction MD. As illustrated in FIG. 12, for example, the substrate assembly 190 may include a portion such that a first process product pitch 340 is adjacent a second process product pitch 340a. The first process product pitch 340 may be greater than or less than the second process product pitch 340a. In another example, the substrate assembly 190 may include a process product pitch 340 that is the same along the length of the substrate assembly. State another way, a first portion of the substrate assembly 190 having a first product pitch 340 may be adjacent to a second portion of the substrate assembly 190 having a second product pitch 340, and the first product pitch is substantially the same as the second product pitch.

As the substrate assembly 190 traverses about the central longitudinal axis 204, heated fluid may be released through the apertures defined by the nozzle plate. As previously discussed, the heated fluid is released through those apertures in the nozzle plate on which a leading edge portion or a tailing edge portion is disposed. For example, a heated fluid may be supplied to a first manifold 266 on which a leading edge portion and a trailing edge portion of the substrate assembly is disposed. Further, a heated fluid may be supplied to a second manifold 268 on which an adjacent, subsequent leading edge portion and trailing edge portion is disposed. However, the heated fluid may not be supplied to the intermediate manifolds 260, which are those manifolds that are located between the first manifold 266 and the second manifold 268. The first and second manifolds 266, 268 may be controlled such that the release of heated fluid occurs when the manifold reaches some radial position about the central longitudinal axis 204. The release of heated fluid may also be timed based on other processes such as in relation to the process of compressing the substrate assembly 190.

For example, the leading edge portion and the trailing edge portion of the substrate assembly 190 may be at least partially melted while traversing about the central longitudinal axis 204. The substrate assembly 190 may then be advanced to an anvil roll 368. The anvil roll 368 may operatively engage at least a portion of the substrate assembly 190. Thus, the anvil roll 368 may be positioned adjacent the nozzle plate 210. The anvil roll 368 includes an anvil roll outer circumferential surface 370 and may be adapted to rotate about an anvil roll axis of rotation 372. The operative engagement of the anvil roll 368 and the external surface 256 of the nozzle plate 210 joins the at least partially melted portion of the one or more overlapping substrates of the substrate assembly 190 forming one or more bonds, as illustrated in FIG. 5E.

It is also to be appreciated that the outer circumferential surface 370 of the anvil roll 368 may rotate at a circumferential velocity. The circumferential velocity may be constant or may be varied as the anvil roll 368 rotates about its axis of rotation 372. The circumferential velocity may be changed according to the size of the substrate assembly so that the anvil roll 368 engages that substrate assembly at the desired location, which may correspond to the intended size of the finished absorbent article or other consumer product. Further, during each rotation of the anvil roll 368, the circumferential velocity may vary. For example, in a single rotation, the rotational velocity may increase and decrease one or more times to position the anvil roll 368 in the desired location to bond the substrate assembly. The anvil roll 368 may be operatively connected to a servo motor (not shown).

The servo motor may operate to change the circumferential velocity of the anvil roll 368.

It is to be appreciated that the anvil roll may alternatively be an anvil block, which traverses linearly to compress at least a portion of the region 336, which includes the leading edge portion and the trailing edge portion, of the substrate assembly 190.

The bonder apparatus 200 may continue to rotate about the central longitudinal axis 204 such that the substrate assembly 190 is advanced to a second guide roll 270. The second guide roll 270 may include a second outer circumferential surface 272 and may be configured to rotate about a second axis of rotation 274. As the second guide roll 270 rotates about the second axis of rotation 274 the substrate assembly 190, which may include a chassis 102, may be transferred from the bonder apparatus 200 to the second outer circumferential surface 272 of the second guide roll 270. The substrate assembly 190 may then be advanced to additional downstream processes.

Figure 14:
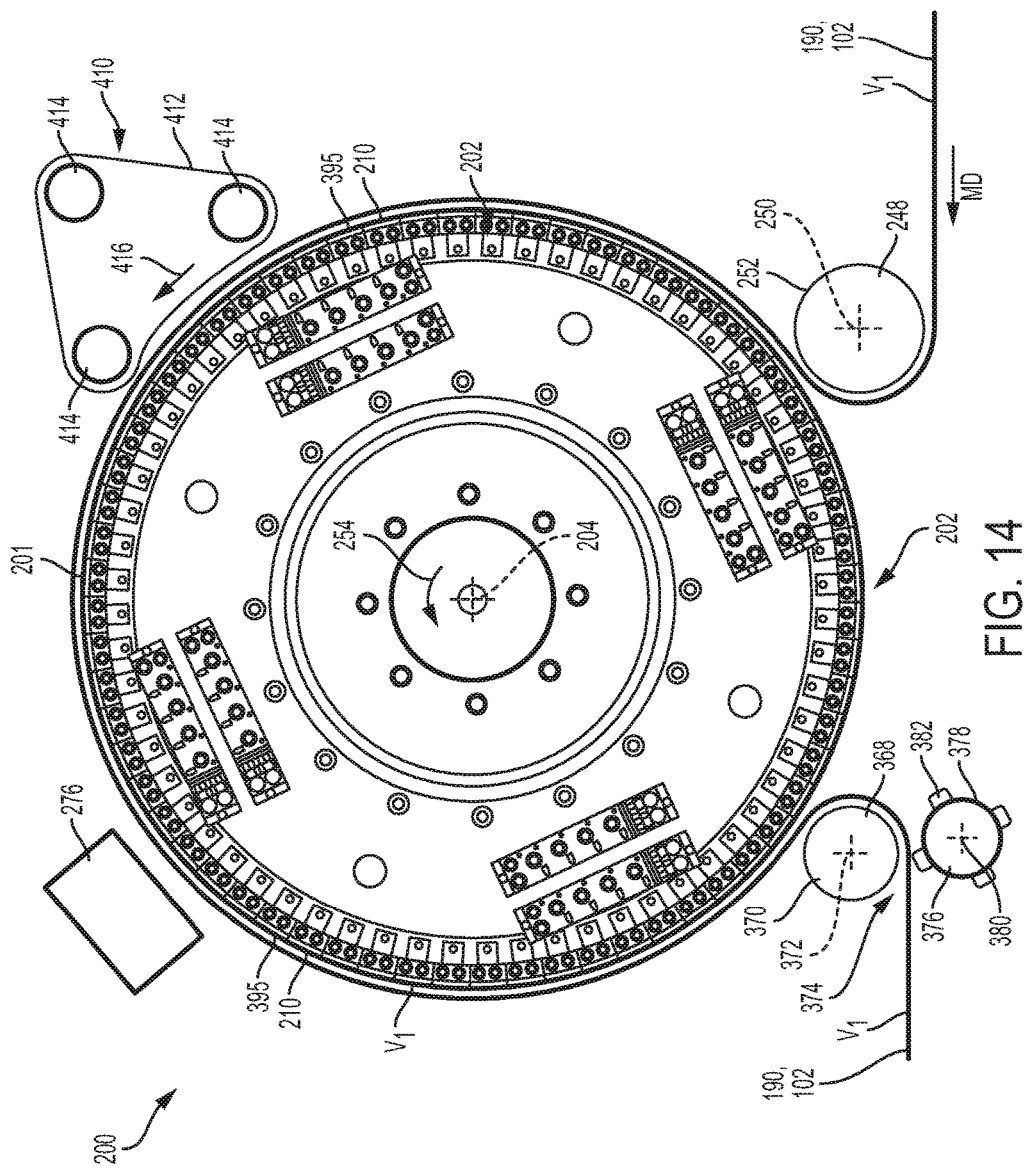
FIG. 14 is an end view of a bonder apparatus in accordance with one non-limiting embodiment of the present disclosure.

Referring to FIG. 14, as the substrate assembly 190 traverses about the central longitudinal axis 204, a position control apparatus 410 may be used to maintain the position of the substrate assembly 190 and/or the chassis 102. In some embodiments, the position control apparatus 410 may include a belt 412, such as a conveyor belt, and two or more rollers 414. The belt 412 may be positioned about a portion of the rollers such that the belt may move in a direction indicated by arrow 416. The position control apparatus 410 may be positioned adjacent the bonder apparatus 200 and may take the shape of at least a portion of the outer circumferential surface 201 of the bonder apparatus 200. The position control apparatus may hold the substrate assembly 190 and/or the chassis 102 in the range of 0 millimeters to about 10 millimeters from the outer circumferential surface 201, or between about 0.5 millimeters to about 5 millimeters from the outer circumferential surface 201. It is to be appreciated that the position control apparatus may be a mechanical apparatus such as clamps or another type of fastener that holds the region 336 of the substrate assembly 190 and/or the chassis 102 in place during the bonding process. Further, a vacuum force, generated by the movement of fluid toward the central longitudinal axis 204, may be used in addition to the mechanical device, or each of the vacuum force and the mechanical device may be applied independently to secure the substrate assembly 109 and/or the chassis 201 against the outer circumferential surface 201 of the bonder apparatus 200. The vacuum force may be generated by pulling air through the plurality of apertures 212 in a direction from the outer circumferential surface 201 toward the central longitudinal axis 204. Alternatively or in addition to the vacuum force generated by the plurality of apertures 212 an external device may direct air toward the outer circumferential surface 201 and/or against the substrate assembly disposed on the outer circumferential surface 201 of the bonder apparatus 200.

A process member 276 may also be placed adjacent the bonder apparatus 200. The process member 276 may be a device that is used to mechanically deform the substrate assembly 190 and/or the chassis 102 in some manner. For example, the process member 276 may be a device that bonds, cuts, scores, or performs some other mechanical deformation on the substrate assembly 190 and/or the chassis 102. Thus, as the substrate assembly 190 and/or the chassis 102 rotate about the central longitudinal axis 254, one or more additional processes may be performed by one or more process members 276. It is to be appreciated that more than one process member 276 may be positioned adjacent to the bonder apparatus 200.

Still referring to FIG. 14, as previously discussed, the leading edge portion and the trailing edge portion of the substrate assembly 190 may be at least partially melted by heated fluid that is released by the groups of apertures corresponding to the position of the leading edge portion and the trailing edge portion of the substrate assembly 190. After the leading edge portion and the trailing edge portion of the substrate assembly 190 have undergone at least a partial melting, the substrate assembly 190 may be transferred from or removed from the outer circumferential surface 201 of the bonder apparatus 200. The substrate assembly 190 may traverse onto an anvil roll 368. The anvil roll 368 may include an outer circumferential surface 370 and be configured to rotate about an axis of rotation 372. The substrate assembly 190 may advance onto the outer circumferential surface 370 of the anvil roll 368. The anvil roll 368 may be positioned adjacent a bond roll 376 forming a nip 374 therebetween. The anvil roll 368 may be configured to operatively engage at least a portion of the bond roll 376. The bond roll 376 may be configured to rotate about an axis of rotation 380 and may include an outer circumferential surface 378. The bond roll 376 may be configured to rotate such that the outer circumferential surface of the bond roll rotates at a variable speed to account for changes in the substrate assembly 190. Further, one or more pressure applying members 382 may extend radially outward from the outer circumferential surface 378 of the bond roll 376. The substrate assembly 190 may advance through the nip 374 between the bond roll 376 and the anvil roll 368. The pressure applying members 382 of the bond roll 376 may engage the outer circumferential surface 370 of the anvil roll 368 causing a portion of the substrate assembly 190 to compress and forming a bond between one or more layers of the substrate assembly 190. The bond roll 376 may be configured such that the pressure applying members 382 are appropriately spaced to engage the leading edge portion and the trailing edge portion that have been at least partially melted by the heated fluid.

More specifically, the outer circumferential surface 378 of the bond roll 376 may rotate at a circumferential velocity. The circumferential velocity may be constant or may be varied as the bond roll 376 rotates about its axis of rotation 380. The circumferential velocity may be changed according to the size of the substrate assembly so that the bond roll 376 engages that substrate assembly at the desired location, which may correspond to the intended size of the finished absorbent article or other consumer product. Further, during each rotation of the bond roll 376, the circumferential velocity may vary. For example, in a single rotation, the rotational velocity may increase and decrease one or more times to position the bond roll 376 in the desired location to bond the substrate assembly. The bond roll 376 may be operatively connected to a servo motor (not shown). The servo motor may operate to change the circumferential velocity of the bond roll 376. The anvil roll 368 may rotate at a constant circumferential velocity and may be configured to operatively engage the bond roll 376.

It is to be appreciated that the substrate assembly is compressed by the one or more pressure applying member while the meltable components of the substrate assembly are at least partially melted, and/or in a tacky state. The temperature of the pressure applying members may be at least below the melting point of the region 336. However, the pressure applying member may be heated. The tackiness property of the meltable components permits the joining of substrate layers, which may include a first substrate 406 and a second substrate 408 or an overlap portion of a single substrate. The pressure applying members may be designed according to aesthetic criteria, for example, to provide discrete, shaped bonds where substrate layers are joined, as illustrated in FIG. 5E. Discrete bonds may also make the seam easier to open, if desired. The discrete bonds may generally take the shape and spacing of the pressure applying surfaces. As one example, the pressure applying members may be generally oval, or may have any other geometric or decorative shape consistent with the desired removal force. The pressure applying members may be regularly or irregularly spaced, and may be oriented in various directions. After being compressed, the substrate assembly 190 may exit the nip 374, as illustrated in FIG. 14, and continue to additional downstream processes.

As previously discussed, the substrate assembly 190 may be positioned such that the leading edge portion and the trailing edge portion are disposed on one or more groups of apertures. The leading edge portion and the trailing edge portion are to be disposed on one or more groups of apertures such that these portions of the substrate assembly may be at least partially melted and joined. However, it is to be appreciated that the aforementioned bonder apparatus 200 may be constrained as to the sizes of substrate assemblies that can be processed on the bonder apparatus 200. More specifically, the bonder apparatus 200 may comprise a certain number of manifolds and each of these manifolds may be configured with groups of apertures, these groups of apertures are spaced from one another at a certain distance. Thus, only substrate assemblies having a certain process product pitch may be acted upon using the bonder apparatus 200. Thus, to accommodate a larger range of substrate assemblies, the substrate assembly 190 may be condensed or expended prior to being disposed on the outer circumferential surface 201 of the bonder apparatus 200.

Figure 15:
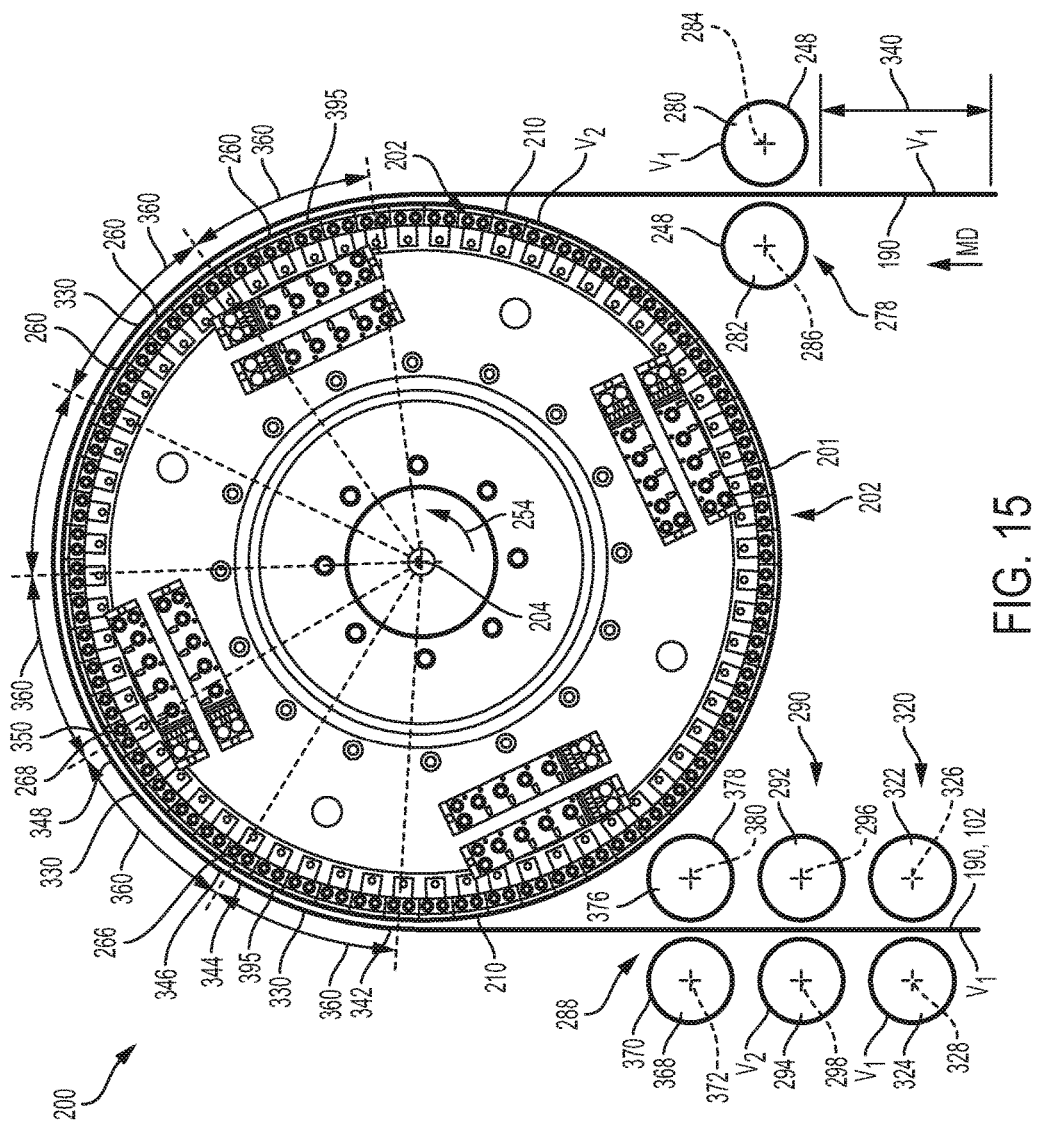
FIG. 15 is an end view of a bonder apparatus in accordance with one non-limiting embodiment of the present disclosure.

As illustrated in FIG. 15, various metering assemblies may be used to change the speed of the substrate assembly and, thus, condense or expand the substrate assembly. For example, a first metering assembly 278 may be positioned adjacent the outer circumferential surface 201 of the bonder apparatus 200. The first metering assembly 278 may include a first metering roll 280 and a second metering roll 282. The first metering assembly 278 may be configured to receive the substrate assembly 190, which may or may not include the chassis 102. The substrate assembly 190 advances in the machine direction MD toward the bonder apparatus 200 at a first velocity $V_1$. The first metering assembly 278 accepts the substrate assembly at a first velocity $V_1$. More specifically, the first metering roll 280 and the second metering roll 282 are configured to rotate about a first metering axis of rotation 284 and a second metering axis of rotation 286, respectively. The first metering roll 280 and the second metering roll 282 rotate about their respective axes of rotation at a first velocity $V_1$, or the velocity at which the substrate assembly 190 is advanced toward the metering assembly 256. However, the bonder apparatus 200 may rotate about the axis of rotation 206 at a slower velocity. The bonder apparatus 200 may rotate about the axis of rotation 206 at a second velocity $V_2$. The second velocity $V_2$ may be less than the first velocity $V_1$. Consequently, the substrate assembly 190 may contract as the substrate assembly 190 exits the first metering assembly 256 and is disposed on the outer circumferential surface 201 of the bonder apparatus 200.

As the substrate assembly 190 advances onto to bonder apparatus 200, the substrate assembly 190 may be relaxed such that the process tension is decreased to a relaxed tension. It is to be appreciated that the substrate assembly may include one or more elastic strands or a substrate which is elastically extensible. Thus, when tension is applied to the substrate assembly, the substrate assembly may extend in the direction in which the tension is applied; further, when the tension is reduced or removed the substrate assembly may relax and contract from the extended state. It is also to be appreciated that a substrate assembly may not include elastic stands and/or an elastic substrate. An inelastic substrate assembly may still be relaxed such that the nonwoven or other inelastic material may gather on the outer circumferential surface 201.

When the bonder apparatus 200 rotates about the central longitudinal axis 204 at a velocity which is different than the velocity of the substrate assembly 190 as the substrate assembly 190 advances to the first metering assembly 278, the substrate assembly 190 may expand or contract. Thus, when the substrate assembly 190 advances onto the bonder apparatus 200, the leading edge portion and the trailing edge portion separated from the leading edge portion by the central portion 330 may be separated by a product arc length 360. The product arc length 360 is the distance between the leading edge portion and the trailing edge portion measured along the outer circumferential surface 201 and across the central portion 330. The product arc length 360 may be less than the process product pitch 340, 340*a* when the bonder apparatus 200 rotates at a velocity less than the velocity of the substrate assembly 190 as the substrate assembly advances to the first metering assembly 278. The product arc length 360 may be greater than the process product pitch 340, 340*a* when the bonder apparatus 200 rotates at a velocity greater than the velocity of the substrate assembly 190 as the substrate assembly advances to the first metering assembly 278.

The expanded or contracted substrate assembly 190 may be at least partially melted as previously described. Further, additional processes may be performed on the substrate assembly 190 and/or the chassis as the expanded or contracted substrate assembly 190 is transferred by the bonder apparatus 200.

However, some processes are best preformed wherein the portion of the substrate assembly 190 to be processed is maintained at the process tension or the process product pitch. Thus, the central portion 330 of the substrate assembly 190, which is the portion of the substrate assembly between each of the adjacent regions 336, as illustrated in FIGS. 13A-13D, may be disposed on the intermediate manifolds 260 or portions thereof. As the substrate assembly 190 is transferred onto the plurality of manifolds 202, which rotate about the axis of rotation 204, the substrate assembly 190 may maintain the same process tension while disposed on the bonder apparatus 200 as the process tension of the substrate assembly 190 while being advanced toward the bonder apparatus 200, or the tension of central portion of the substrate assembly, which is the portion between adjacent regions, may be decreased to a relaxed tension, which is less than the process tension. However, while the tension of the central portion may be decreased to a relaxed tension, the tension on each region may be maintained at the process tension. Further, as the substrate assembly 190 rotates about the axis of rotation 206, the product arc length 360 may be substantially the same as the process product pitch, or the product arc length 240 may be less than or greater than the process product pitch 340, 340*a*.

Figure 16A:
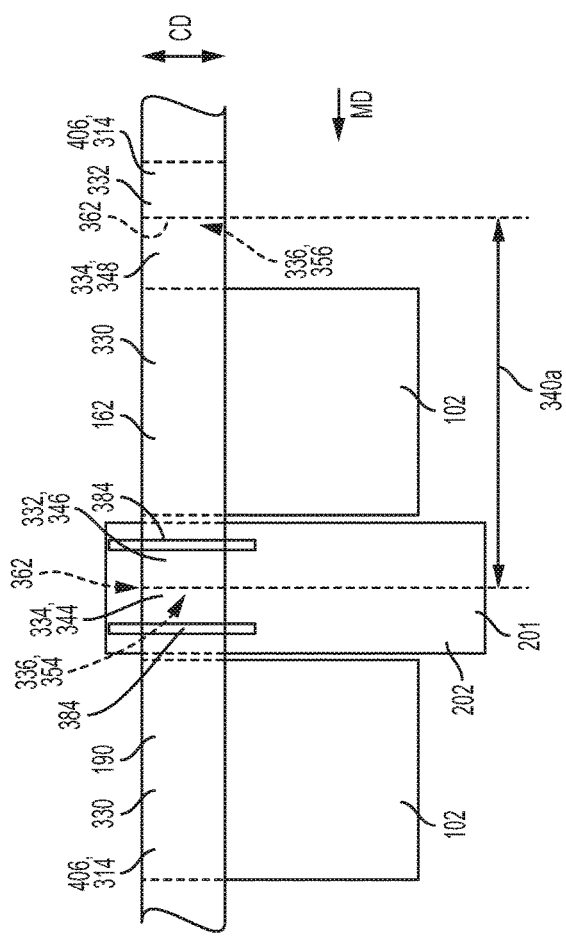
FIG. 16A is a top view of a substrate assembly including a chassis disposed on a portion of a bonder apparatus in accordance with one non-limiting embodiment of the present disclosure.
Figure 16B:
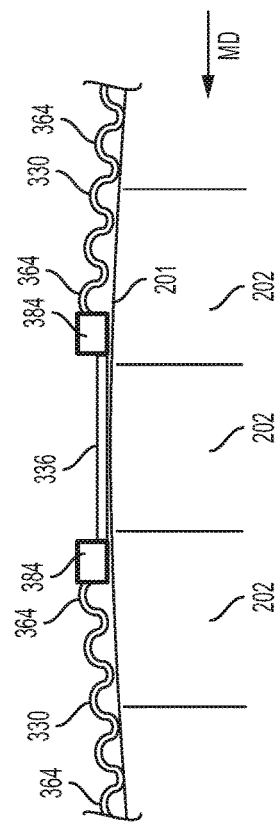
FIG. 16B is a side view of a substrate assembly disposed on a portion of the bonder apparatus in accordance with one non-limiting embodiment of the present disclosure.

For example, bonding may be best preformed when the portion of the substrate assembly to be bonded is maintained at the process tension or, stated another way, the portion of the substrate assembly to be bonded is under sufficient tension to prevent puckering of the substrate assembly. When the tension of the substrate assembly 190 is reduced from a process tension to a relaxed tension, the elastics in the substrate assembly 190 contract and/or the substrate assembly gathers. This allows the substrates to form one or more puckers 364, as illustrated in FIG. 16B. Processing a substrate assembly having a configuration including one or more puckers 364 may lead to the production of a poor quality absorbent article. For example, the gathered configuration including one or more puckers may result in the bond being placed in the wrong position on the substrate assembly or the bond including more layers of substrate than intended, which may result in a weak bond. Similarly, the gathered configuration may result in inaccurate cutting or scoring of the substrate assembly 190.

To maintain the process tension of the region 336, various position control devices may be used. For example, the plurality of apertures 212 may be configured to transfer fluid, such as air, through the apertures 212 in a direction toward the axis of rotation 204 causing the substrate assembly 190 to be secured to the outer circumferential surface 201 with a vacuum force. In another example, a mechanical device may be used to apply a mechanical force to secure the substrate assembly 190 to the outer circumferential surface 201. For example, the bonder apparatus 200 may include a clamping device 384, as illustrated in FIGS. 16A and 16B. The clamping device 384 may be configured to engage a portion of the substrate assembly 190 adjacent to or within the region 336. Further, a position control apparatus, such as that illustrated in FIG. 14, oriented adjacent to the bonder apparatus may be used to secure the substrate assembly 190 to the bonder apparatus 200.

As illustrated in FIG. 15, the substrate assembly 190 may be rotated at a second velocity $V_2$, which may be greater than or less than the first velocity $V_1$. During rotation of the substrate assembly 190 one or more process may mechanically deform one or more portions of the substrate assembly 190, as previously discussed.

Upon completion of the one or more processes, the substrate assembly 190 may be removed from the outer circumferential surface 201 of the bonder apparatus 200. The substrate assembly 190 may advance to a compression assembly 288. The compression assembly 288 may include an anvil roll 368 and a bond roll 376. The anvil roll 368 may include an outer circumferential surface 370 and may be configured to rotate about an axis of rotation 372. The bond roll 376 may include an outer circumferential surface 378 and may be configured to rotate about an axis of rotation 380. The anvil roll 368 and the bond roll 376 operatively engage to bond at least a portion of the substrate assembly 190. It is to be appreciated that the substrate assembly 190 may be compressed while disposed on the bonder apparatus 200, as previously discussed.

The substrate assembly 190 may advance through a second metering assembly 290. The second metering assembly 290 may include a third metering roll 292 and a fourth metering roll 294. The third metering roll 292 may rotate about a third metering axis of rotation 296 and the fourth metering roll 294 may rotate about a fourth metering axis of rotation 298. The third metering roll 292 and the fourth metering roll 294 rotate at the second velocity $V_2$. The substrate assembly 190 advances toward the second metering assembly 290 at a second velocity $V_2$. The second metering assembly 290 may ensure that the substrate assembly 190 continues to advance at the second velocity $V_2$ as the substrate assembly 190 passes through the compression assembly 288.

The substrate assembly 190 may continue to advance at the second velocity $V_2$ or the speed of the substrate assembly 190 may be changed by a third metering assembly 320. Downstream of the second metering assembly 242 may be a third metering assembly 320, as illustrated in FIG. 12. The substrate assembly 190 may advance at the second velocity $V_2$ between the second metering assembly 242 and the third metering assembly 290. The third metering assembly 290 may include a fifth metering roll 322 and a sixth metering roll 324 that are each configured to rotate about a fifth metering axis of rotation 326 and a sixth metering axis of rotation 328, respectively. The third metering assembly 320 may be configured to return the substrate assembly 190 to the first velocity $V_1$. Thus, the fifth metering roll 322 and the sixth metering roll 324 may each rotate about their respective axes of rotation 326, 328 at the first velocity $V_1$. The substrate assembly 190 may advance away from the third metering assembly 320 at the first velocity $V_1$. Further, the third metering assembly 320 may expand the substrate assembly 190 to the process tension, which is the process tension of the substrate assembly 190 prior to advancing through the first metering assembly 278. It is to be appreciated that the velocity may be changed such that the process tension is different when the substrate assembly 190 advances through the third metering assembly.

It is also to be appreciated that the metering assembly may be any configuration of rolls and/or conveyors that allows the tension on the substrate assembly to be isolated on either side of the metering assembly. Examples of metering assemblies may include a vacuum conveyor, one or more rollers positioned to s-wrap the substrate assembly, one or more driven rolls, and/or a vacuum roll.

Further, the compression assembly 288 may be positioned downstream of the second metering assembly 290 and the third metering assembly 320. Thus, the substrate assembly 190 may undergo a change in velocity prior to being compressed by the compression assembly 288 forming one or more bonds between the layers of the substrate assembly 190.

It is to be appreciated that the metering devices may also be configured to expand the substrate assembly 190 prior to the substrate assembly being disposed on the bonder apparatus 200. The amount of expansion of the substrate assembly 190 may depend on the elastic or inelastic properties of the substrate material and/or the elastic components of the substrate assembly.

The expansion and contraction of the substrate assembly 190 allows for a greater number of sizes to be processed on the same bonder apparatus 200. The properties of the web in combination with the number of manifolds disposed at the central longitudinal axis allow manufacturers to produce a wide range of sizes of absorbent articles on a single bonder apparatus 200.

As previously discussed, a fluid is heated to a temperature sufficient to at least partially melt at least a portion of the region 336, which includes the leading edge portion and trailing edge portion, of the substrate assembly 190. The apertures 212 defined by the nozzle plate 210 direct a jet of the heated fluid onto at least a portion of the region 336 of the substrate assembly 190, which may include a first substrate 406 and a second substrate 408. The heated fluid partially melts at least a portion of the region 336. As the bonder apparatus 200 continues to rotate about the axis of rotation 204, an anvil roll may compress the partially melted overlap portion against the outer circumferential surface 201 of the bonder apparatus. Alternatively, the substrate assembly 190 may be transferred from the bonder apparatus 190 and advance through a compression assembly. The anvil roll and bond roll, which may include one or more press members, then compresses the partially melted overlap area creating one or more discrete bond sites 336a in the overlap area 362, as shown in FIG. 5E, between the first and second substrates.

It is to be appreciated that by applying different amounts of force in different locations, it may be possible to bond through different numbers of substrate layers or materials along the region. By selectively compressing portions with more or less force, portions of the substrates with fewer layers or different materials will not be over compressed and portions of the substrates with more layers or different materials will not be under compressed. In some embodiments, the compression assembly may include different shaped projections, or may have different configurations of projections.

In some embodiments, the press member may compress the partially melted overlap area against the anvil roll outer circumferential surface at a pressure in the range of about $1\times10^5$ Newtons per square meter to about $1\times10^8$ Newtons per square meter. In some embodiments, the press member 366 may compress the first and second belt substrates for a time period ranging from about 1 millisecond to about 3 milliseconds or from about 3 milliseconds to about 10 milliseconds or from about 10 milliseconds to about 1000 milliseconds or greater. Shorter or longer time intervals may be used.

Figure 17A:
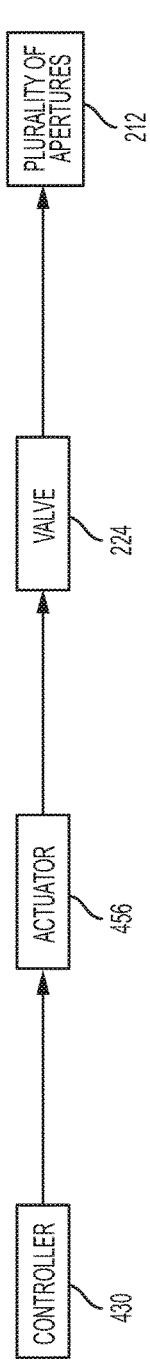
FIG. 17A is a schematic representation of the communication of a controller in accordance with one non-limiting embodiment of the present disclosure.

Each first control chamber opening 464 defined by the end portion 462 of the manifold 202 may be operatively connected to an actuator 456, as illustrated in FIGS. 6, 8, and 10. The actuator 456 engages the valve 224. The valve 224 may be positioned in an open configuration, which causes the engagement member 470 to be positioned in a second configuration such that fluid flows through the fluid opening 458, into the control chamber 460, and into the fluid chamber 468, or a closed configuration, which causes the engagement member 470 to be positioned in a first configuration, which prevents fluid from being supplied to the fluid opening 458 and/or the fluid chamber 468. A controller 430 may be any device that passes a signal to the actuator that is used to control the position of the valve. An example of a controller 430 may include a programmable logic controller (PLC) or other control computer that may be a stand-alone system or part of an overall control system. Generally, the valve is controlled by providing an on signal to the actuator to place the valve in an open position or an off signal to place the valve in a closed position. The controller may pass an on or off signal at an exact predetermined time. This allows for precise and accurate control of the valve. The controller may also account for performance speed of the valve, by varying the on and off signal timing to account for the activation time of the valve. The controller 430 may control one or more valves 224. The controller 430 may communicate either an open position or a close position to the valve 224, as illustrated in FIG. 17A, for example. The open or closed configuration may depend on the placement of the substrate assembly 190 on the bonder apparatus 200, as previously discussed. The valve 224 may then be connected to a single, engagement member 470 which slidably engages the control chamber 460 of a manifold 202. If the valve 224 is positioned in the open position, the fluid will ultimately pass through the plurality of apertures defined by the nozzle plate. If the valve is positioned in the closed position, no fluid will pass through the plurality of apertures.

Figure 17B:
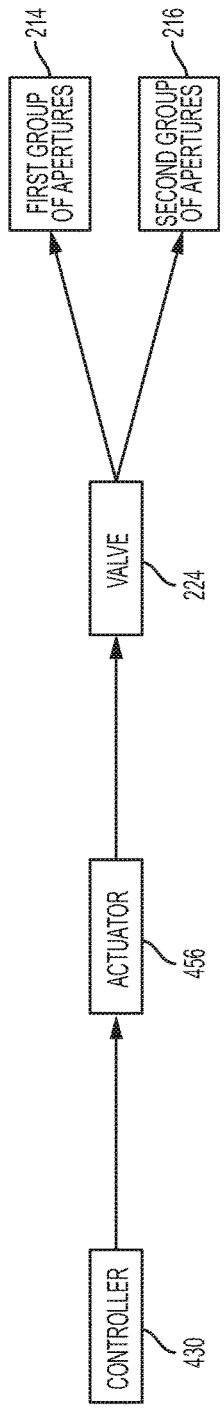
FIG. 17B is a schematic representation of the communication of a controller in accordance with one non-limiting embodiment of the present disclosure.

In another example, the controller 430 may control a valve operatively connected to a first group of apertures 214 and a second group of apertures 216, as illustrated in FIG. 17B. Because a single valve controls both groups of apertures, when the valve is positioned in an open position, fluid may be supplied to both the first group of apertures 214 and the second group of apertures 216. Similar to the above, when the valve 224 is in a closed configuration, no fluid will pass through the control chamber and, thus, no fluid is supplied to the first group of apertures 214 and a second group of apertures 216.

Figure 17C:
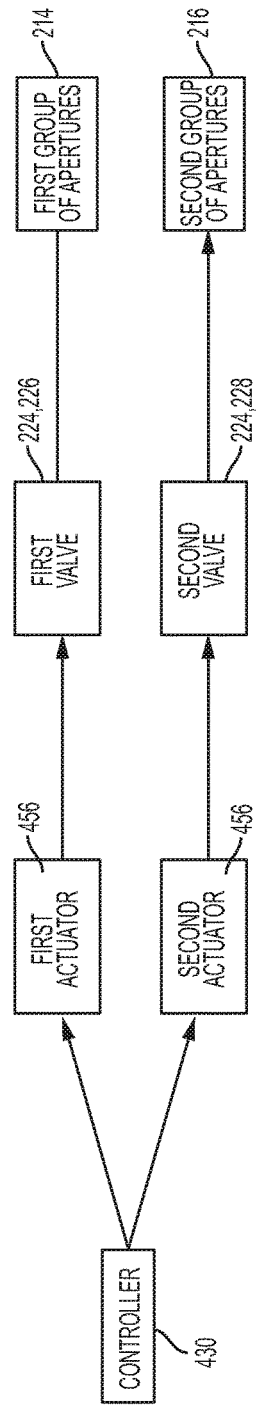
FIG. 17C is a schematic representation of the communication of a controller in accordance with one non-limiting embodiment of the present disclosure.

In yet another example, as illustrated in FIG. 17C, the controller 430 may communicate with more than one actuator, and each actuator may engage a valve. The controller 430 may configure the first valve 226 to be in either an open position, such that fluid passes to a first group of apertures 214, or a closed position, such that no fluid passes to first group of apertures 214. Further, independent of the first valve 226, the controller 430 may configure the second valve 228 to be in an open position, such that fluid passes to the second group of apertures 216, or a close position, such that no fluid passes to the second group of apertures 216. Thus, a single manifold may include a first group of apertures fluidly connected to a first control chamber and a second group of apertures fluidly connected to a second control chamber. Depending on the control of the first valve and the second valve, fluid may exit through only the first group of apertures and not through the second group of apertures, or vice versa. It is also to be appreciated that the first and second valves may simultaneously be positioned in the open position such that fluid passes to both the first group of apertures and the second group of apertures. Similarly, both the first and the second valves may simultaneously be positioned in the closed position. It is to be appreciated that the manifold may include any number of groups of apertures and each of the groups of apertures may be operatively connected to a valve that is controlled by the controller. For example, the manifold may include a third and fourth groups of apertures that are fluidly connected to a third and fourth valve, respectively.

It is also to be appreciated that the valve 224 and actuator 456 may be placed prior to the fluid entering the manifold 202, as previously discussed, or after the fluid has been released within the manifold 202.

In some embodiments, a method for forming a bond in a substrate assembly 190 may include the steps of rotating the bonder apparatus 200 about an axis of rotation 204. The bonder apparatus 200 includes a plurality of manifolds 202 disposed about a central longitudinal axis 204 and configured to rotate about the central longitudinal axis 204. The first substrate assembly 190 may be advanced in a machine direction. The first substrate assembly 190 may include a first process product pitch, wherein the first product pitch is defined by a first leading portion and a first trailing portion, and a first central portion between the first leading portion and the first trailing portion. Further, the first substrate assembly includes a first surface and a second surface opposite the first surface. The substrate assembly 190 may be advanced onto the bonder apparatus such that the first surface of the first substrate assembly is in facing relationship with the plurality of manifolds 202. More specifically, the first leading portion of the first substrate assembly may be received on a first manifold of the plurality of manifolds. Further, the first trailing portion of the first substrate assembly may be received on a second manifold of the plurality of manifolds. The first manifold and the second manifold may be separated by a first product arc length. The first central portion of the first substrate assembly may be disposed on one or more manifolds between the first manifold and the second manifold. A fluid may be passed to or directed toward the first manifold and the second manifold. The fluid may be heated by a heat source, which is external to the plurality of manifolds. The fluid may be heated to a temperate sufficient to at least partially melt the substrate assembly. Further, the temperature of the heated may also take into account any heat loss that may occur as the heat fluid is transferred to the manifolds. The heated fluid may be released through a first plurality of apertures of the first manifold such that the heated fluid engages the first leading portion. The heated fluid may also be released through a second plurality of apertures of the second manifold such that the heated fluid engages the first trailing portion. At least a portion of the first leading portion and the first trailing portion of the first substrate assembly may be bonded while rotating on the bonder apparatus 200 or after being removed from the bonder apparatus 200.

It is to be appreciated that the heated fluid may be release through one or more slots defined by the support plate of the first manifold such that the heated fluid engages the leading portion. Similarly, the heated fluid may be release through one or more slots defined by the support plate of the second manifold such that the heated fluid engages the trailing portion.

In some embodiments, a method for forming a bond in a substrate assembly 190 may include the steps of rotating the bonder apparatus 200 about an axis of rotation 204. The bonder apparatus 200 includes a plurality of manifolds 202 disposed about a central longitudinal axis 204 and configured to rotate about the central longitudinal axis 204. The first substrate assembly 190 may be advanced in a machine direction. The first substrate assembly 190 may include a first process product pitch, wherein the first product pitch is defined by a first leading portion and a first trailing portion, and a first central portion between the first leading portion and the first trailing portion. Further, the first substrate assembly includes a first surface and a second surface opposite the first surface. The substrate assembly may be expanded or contracted such that the substrate assembly is advanced at a second process product pitch, wherein the second process product pitch is greater than or less than the first process product pitch. The substrate assembly may be expended or contracted so that the leading portion and the trailing portion are received on the manifold such that the leading portion and the trailing portion are disposed on the groups of apertures. After expanding or contracting the substrate assembly, the substrate assembly 190 may be advanced onto the bonder apparatus such that the first surface of the first substrate assembly is in facing relationship with the plurality of manifolds 202. More specifically, the first leading portion of the first substrate assembly may be received on a first manifold of the plurality of manifolds. Further, the first trailing portion of the first substrate assembly may be received on a second manifold of the plurality of manifolds. The first manifold and the second manifold may be separated by a first product arc length. The first central portion of the first substrate assembly may be disposed on one or more manifolds between the first manifold and the second manifold. A fluid may be passed to or directed toward the first manifold and the second manifold. The fluid may be heated by a heat source, which is external to the plurality of manifolds. The fluid may be heated to a temperate sufficient to at least partially melt the substrate assembly. Further, the temperature of the heated may also take into account any heat loss that may occur as the heat fluid is transferred to the manifolds. The heated fluid may be released through a first group of apertures, which may be substantially surrounded by a first slot, of the first manifold such that the heated fluid engages the leading portion. Further, the heat fluid may be released through a first group of apertures, which may be substantially surrounded by a second slot, of the second manifold such that the heated fluid engages the trailing portion. After the portions of the substrate assembly are at least partially melted by the heat fluid, the substrate assembly may bonded in those portions. The bonding may be performed while the substrate assembly is disposed on the plurality of manifolds, or after the substrate assembly has been transferred from or removed from the bonder apparatus.

The substrate assembly 190 may undergo one or more processes while being transferred by the bonder apparatus 200. For example, the substrate assembly 190 may undergo cutting, such as with a cutting mechanism. The cutting mechanism may be a laser, a knife, or an ultrasonic cutting device, such as an ultrasonic processes system as disclosed in European Patent Application No. 2796271A1. In some embodiments, the process assembly 220 may include a seaming station 548, such as disclosed in U.S. Pat. No. 8,778,127 and U.S. Patent Publication Nos. 2014/0110053; 2014/0305593; and 2013/0218116.

This application claims the benefit of U.S. Provisional Application No. 62/265,443 filed on Dec. 10, 2015 and U.S. Provisional Application No. 62/300,114 filed on Feb. 26, 2016, the entirety of which are incorporated by reference herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for forming a bond, the method comprising the steps of:
   advancing a substrate assembly in a machine direction, wherein the substrate assembly comprises a process product pitch defined by a leading portion and a trailing portion, and a central portion between the leading portion and the trailing portion;

rotating a bonder apparatus about an axis of rotation, wherein the bonder apparatus comprises a plurality of manifolds disposed about a central longitudinal axis, wherein the plurality of manifolds comprise a first manifold, as second manifold, and one or more manifolds disposed between the first manifold and the second manifold, and wherein each of the plurality of manifolds comprises a support plate and a nozzle plate adjacent the support plate, wherein the nozzle plate defines a plurality of apertures;

receiving the leading portion of the substrate on the support plate of the first manifold;

receiving the trailing portion of the substrate on the support plate of the second manifold, wherein the central portion of the substrate is disposed on the support plates of the one or more manifolds disposed between the first manifold and the second manifold;

heating a fluid to form a heated fluid;

supplying the heated fluid to the plurality of manifolds;

releasing the heated fluid through the plurality of apertures defined by the nozzle plate of the first manifold such that the heated fluid engages the leading portion;

releasing the heated fluid through the plurality of apertures defines by the nozzle plate of the second manifold such that the heated fluid engages the trailing portion; and bonding at least a portion of the substrate assembly.

2. A method for forming a bond, the method comprising the steps of:

advancing a substrate assembly in a machine direction at a process product pitch, wherein the substrate assembly comprises a process product pitch defined by a leading portion and a trailing portion, and a central portion between the leading portion and the trailing portion;

rotating a bonder apparatus about an axis of rotation, wherein the bonder apparatus comprises a plurality of manifolds disposed about a central longitudinal axis, wherein the plurality of manifolds comprises a first manifold, as second manifold, and one or more manifolds disposed between the first manifold and the second manifold, and wherein each of the plurality of manifolds includes a nozzle plate defining a plurality of apertures;

expanding or contracting the substrate assembly such that the substrate assembly is advanced at a second process product pitch, wherein the second process product pitch is greater than or less than the process product pitch;

receiving the leading portion of the substrate on the first manifold;

receiving the trailing portion of the substrate on the second manifold, wherein the central portion of the substrate is disposed on the one or more manifolds disposed between the first manifold and the second manifold;

heating a fluid to form a heated fluid;

supplying the heated fluid to the plurality of manifolds;

releasing the heated fluid through the plurality of apertures defined by the nozzle plate of the first manifold such that the heated fluid engages the leading portion;

releasing the heated fluid through the plurality of apertures defined by the nozzle plate of the second manifold such that the heated fluid engages the trailing portion; and bonding at least a portion of the substrate assembly.

* * * * *